US012636118B2

(12) United States Patent
Paul et al.

(10) Patent No.: US 12,636,118 B2
(45) Date of Patent: May 26, 2026

(54) MRI COMPATIBLE INTERVENTIONAL MEDICAL DEVICES AND RELATED METHODS

(71) Applicants:Muffin Incorporated, West Lafayette, IN (US); Cook Medical Technologies LLC, Bloomington, IN (US)

(72) Inventors: Ram H. Paul, Bloomington, IN (US); Sean D. Chambers, Bloomington, IN (US); David Gross, Lafayette, IN (US); Neal Fearnot, West Lafayette, IN (US); Jesse Roll, West Lafayette, IN (US); Joshua F. Krieger, Topsfield, MA (US); Carl A. Cook, Bloomington, IN (US)

(73) Assignees: Muffin Incorporated, West Lafayette, IN (US); Cook Medical Technologies LLC, Bloomington, IN (US)

( * ) Notice: Subject to any disclaimer, the term of this patent is extended or adjusted under 35 U.S.C. 154(b) by 253 days.

(21) Appl. No.: 18/234,440

(22) Filed: Aug. 16, 2023

(65) Prior Publication Data

US 2024/0058094 A1     Feb. 22, 2024

Related U.S. Application Data

(60) Provisional application No. 63/398,358, filed on Aug. 16, 2022.

(51) Int. Cl.
*A61B 90/00*          (2016.01)
*A61B 5/055*          (2006.01)
(Continued)

(52) U.S. Cl.
CPC .............. *A61B 90/39* (2016.02); *A61B 5/055* (2013.01); *A61L 31/022* (2013.01); *A61L 31/14* (2013.01);
(Continued)

(58) Field of Classification Search
CPC . A61B 90/39; A61B 5/055; A61B 2090/3954; A61M 25/09; A61M 2025/09075; A61L 31/022; A61L 31/14
See application file for complete search history.

(56) References Cited

U.S. PATENT DOCUMENTS

| | | | |
|---|---|---|---|
| 4,471,204 A | 9/1984 | Takafuji | |
| 4,781,186 A | 11/1988 | Simpson | |

(Continued)

FOREIGN PATENT DOCUMENTS

| | | | |
|---|---|---|---|
| AT | 312640 | 12/2005 | |
| AU | 2002334881 | 4/2003 | |

(Continued)

OTHER PUBLICATIONS

U.S. Office Action (Non-Final Rejection) U.S. Appl. No. 18/238,747, dated Jul. 1, 2025.
(Continued)

*Primary Examiner* — Chao Sheng
(74) *Attorney, Agent, or Firm* — MacMillan, Sobanski & Todd, LLC

(57)          ABSTRACT
The disclosure relates to methods of imaging a portion of a body vessel using magnetic resonance imaging (MRI), methods of performing interventional medical treatment under MRI, interventional medical devices, such as wire guides, useful in performing treatment under MRI, and methods of making interventional medical devices. A method of imaging a portion of a body vessel of a patient using MRI includes advancing through a body vessel an end of a wire guide comprising a continuous metal core member and a continuous jacket disposed over the entire core member through a body vessel and scanning the portion of the patient that is positioned within an MRI scanner and that includes a portion of the body vessel within which the end of the wire guide is disposed. A secondary medical device, (Continued)

such as a catheter, can be disposed over the wire guide and manipulated in the method.

20 Claims, 11 Drawing Sheets

(51) Int. Cl.
    *A61L 31/02*     (2006.01)
    *A61L 31/14*     (2006.01)
    *A61M 25/09*     (2006.01)
(52) U.S. Cl.
    CPC ................ *A61B 2090/3954* (2016.02); *A61M 2025/09075* (2013.01)

(56) References Cited

U.S. PATENT DOCUMENTS

| | | | |
|---|---|---|---|
| 4,862,891 A | 9/1989 | Smith |
| 5,053,004 A | 10/1991 | Markel |
| 5,169,396 A | 12/1992 | Dowlatshahi |
| 5,228,441 A | 7/1993 | Lundquist |
| 5,284,128 A | 2/1994 | Hart |
| 5,291,890 A | 3/1994 | Cline |
| 5,315,996 A | 5/1994 | Lundquist |
| 5,322,064 A | 6/1994 | Lundquist |
| 5,322,505 A | 6/1994 | Krause |
| 5,329,923 A | 7/1994 | Lundquist |
| 5,346,473 A | 9/1994 | Bowman |
| 5,362,478 A | 11/1994 | Desai |
| 5,425,723 A | 6/1995 | Wang |
| 5,454,787 A | 10/1995 | Lundquist |
| 5,460,187 A | 10/1995 | Daigle |
| 5,477,856 A | 12/1995 | Lundquist |
| 5,507,766 A | 4/1996 | Kugo |
| 5,573,520 A | 11/1996 | Schwartz |
| 5,578,009 A | 11/1996 | Kraus |
| 5,605,543 A | 2/1997 | Swanson |
| 5,685,868 A | 11/1997 | Lundquist |
| 5,690,120 A | 11/1997 | Jacobsen |
| 5,728,079 A | 3/1998 | Weber |
| 5,730,732 A | 3/1998 | Sardelis |
| 5,741,429 A | 4/1998 | Donadio, III |
| 5,755,714 A | 5/1998 | Murphy-Chutorian |
| 5,792,055 A | 8/1998 | Mckinnon |
| 5,810,807 A | 9/1998 | Ganz |
| 5,813,996 A | 9/1998 | Jon |
| 5,833,632 A | 11/1998 | Jacobsen |
| 5,833,692 A | 11/1998 | Cesarini |
| 5,853,375 A | 12/1998 | Orr |
| 5,897,533 A | 4/1999 | Glickman |
| 5,897,536 A | 4/1999 | Nap |
| 5,908,410 A | 6/1999 | Weber et al. |
| 5,916,162 A | 6/1999 | Snelten |
| 5,922,003 A | 7/1999 | Anctil |
| 5,951,494 A | 9/1999 | Wang |
| 6,017,319 A | 1/2000 | Jacobsen |
| 6,019,737 A | 2/2000 | Murata |
| 6,059,769 A | 5/2000 | Lunn |
| 6,093,185 A | 7/2000 | Ellis |
| 6,102,890 A | 8/2000 | Stivland |
| 6,146,373 A | 11/2000 | Cragg |
| 6,228,073 B1 | 5/2001 | Noone |
| 6,246,896 B1 | 6/2001 | Dumoulin |
| 6,246,914 B1 | 6/2001 | De La Rama |
| 6,267,781 B1 | 7/2001 | Tu |
| 6,273,404 B1 | 8/2001 | Holman |
| 6,286,555 B1 | 9/2001 | Pauker |
| 6,350,253 B1 | 2/2002 | Deniega |
| 6,375,059 B2 | 4/2002 | Ohnishi |
| 6,394,976 B1 | 5/2002 | Winston |
| 6,428,489 B1 | 8/2002 | Jacobsen |
| 6,451,026 B1 | 9/2002 | Biagtan |
| 6,458,088 B1 | 10/2002 | Hurtak |
| 6,464,645 B1 | 10/2002 | Park |

| | | | |
|---|---|---|---|
| 6,574,497 B1 | 6/2003 | Pacetti |
| 6,611,720 B2 | 8/2003 | Hata |
| 6,612,998 B2 | 9/2003 | Gosiengfiao |
| 6,613,002 B1 | 9/2003 | Clark et al. |
| 6,623,491 B2 | 9/2003 | Thompson |
| 6,626,849 B2 | 9/2003 | Huitema |
| 6,652,508 B2 | 11/2003 | Griffin |
| 6,675,033 B1 | 1/2004 | Lardo et al. |
| 6,687,533 B1 | 2/2004 | Hirano |
| 6,695,781 B2 | 2/2004 | Rabiner |
| 6,714,809 B2 | 3/2004 | Lee |
| 6,749,560 B1 | 6/2004 | Konstorum |
| 6,772,000 B2 | 8/2004 | Talpade |
| 6,799,067 B2 | 9/2004 | Pacetti |
| 6,845,259 B2 | 1/2005 | Pacetti |
| 6,860,898 B2 | 3/2005 | Stack |
| 6,911,016 B2 | 6/2005 | Balzum |
| 6,918,882 B2 | 7/2005 | Skujins |
| 6,975,896 B2 | 12/2005 | Ehnholm |
| 7,001,369 B2 | 2/2006 | Griffin |
| 7,074,197 B2 | 7/2006 | Reynolds |
| 7,160,296 B2 | 1/2007 | Pearson |
| 7,169,118 B2 | 1/2007 | Reynolds |
| 7,182,735 B2 | 2/2007 | Shireman |
| 7,278,973 B2 | 10/2007 | Iwami |
| 7,347,829 B2 | 3/2008 | Mark |
| 7,507,211 B2 | 3/2009 | Pacetti |
| 7,540,845 B2 | 6/2009 | Parins |
| 7,553,287 B2 | 6/2009 | Reynolds |
| 7,596,402 B2 | 9/2009 | Duerk |
| 7,618,379 B2 | 11/2009 | Reynolds |
| 7,641,621 B2 | 1/2010 | Crank |
| 7,651,578 B2 | 1/2010 | Sharrow |
| 7,708,751 B2 | 5/2010 | Hughes |
| 7,747,314 B2 | 6/2010 | Parins |
| 7,749,264 B2 | 7/2010 | Gregorich |
| 7,758,520 B2 | 7/2010 | Griffin |
| 7,761,138 B2 | 7/2010 | Wang |
| 7,778,682 B2 | 8/2010 | Kumar |
| 7,785,273 B2 | 8/2010 | Eskuri |
| 7,789,906 B2 | 9/2010 | Blank |
| 7,792,568 B2 | 9/2010 | Zhong |
| 7,833,175 B2 | 11/2010 | Parins |
| 7,841,994 B2 | 11/2010 | Skujins |
| 7,848,788 B2 | 12/2010 | Tulley et al. |
| 7,875,025 B2 | 1/2011 | Cockburn |
| 7,914,467 B2 | 3/2011 | Layman |
| 7,918,819 B2 | 4/2011 | Karmarkar |
| 7,943,161 B2 | 5/2011 | Carlgren |
| 7,989,042 B2 | 8/2011 | Obara |
| 7,993,286 B2 | 8/2011 | Reynolds |
| 8,002,715 B2 | 8/2011 | Shireman |
| 8,007,434 B2 | 8/2011 | Olson |
| 8,021,311 B2 | 9/2011 | Munoz |
| 8,048,004 B2 | 11/2011 | Davis |
| 8,048,030 B2 | 11/2011 | Mcguckin, Jr. |
| 8,049,137 B2 | 11/2011 | Holman |
| 8,067,073 B2 | 11/2011 | Zhong |
| 8,070,693 B2 | 12/2011 | Ayala |
| 8,082,021 B2 | 12/2011 | Hyde |
| 8,092,444 B2 | 1/2012 | Lentz |
| 8,105,246 B2 | 1/2012 | Voeller |
| 8,137,292 B2 | 3/2012 | Skujins |
| 8,137,293 B2 | 3/2012 | Zhou |
| 8,142,431 B2 | 3/2012 | Ducharme |
| 8,163,326 B2 | 4/2012 | Zhong |
| 8,167,815 B2 | 5/2012 | Parihar |
| 8,167,821 B2 | 5/2012 | Sharrow |
| 8,182,444 B2 | 5/2012 | Uber, III |
| 8,182,465 B2 | 5/2012 | Griffin |
| 8,211,116 B2 | 7/2012 | Oostman, Jr. |
| 8,211,143 B2 | 7/2012 | Stefanchik |
| 8,214,015 B2 | 7/2012 | Macaulay |
| 8,257,279 B2 | 9/2012 | Davis |
| 8,257,358 B2 | 9/2012 | Haddock |
| 8,262,563 B2 | 9/2012 | Bakos |
| 8,292,827 B2 | 10/2012 | Musbach |
| 8,292,828 B2 | 10/2012 | Uihlein |
| 8,337,492 B2 | 12/2012 | Kunis |

(56)  References Cited

U.S. PATENT DOCUMENTS

| | | |
|---|---|---|
| 8,376,961 B2 | 2/2013 | Layman |
| 8,396,532 B2 | 3/2013 | Jenkins |
| 8,409,114 B2 | 4/2013 | Parins |
| 8,414,506 B2 | 4/2013 | Reynolds |
| 8,419,658 B2 | 4/2013 | Eskuri |
| 8,478,381 B2 | 7/2013 | Kocaturk |
| 8,485,992 B2 | 7/2013 | Griffin |
| 8,521,257 B2 | 8/2013 | Whitcomb |
| 8,523,786 B2 | 9/2013 | Von Weymarn-Scharli |
| 8,526,691 B2 | 9/2013 | Strehl |
| 8,529,872 B2 | 9/2013 | Frank |
| 8,535,243 B2 | 9/2013 | Shireman |
| 8,535,310 B2 | 9/2013 | Hardin, Jr. |
| 8,540,648 B2 | 9/2013 | Uihlein |
| 8,551,020 B2 | 10/2013 | Chen |
| 8,551,021 B2 | 10/2013 | Voeller |
| 8,556,914 B2 | 10/2013 | Vrba |
| 8,620,406 B2 | 12/2013 | Smith |
| 8,636,716 B2 | 1/2014 | Griffin |
| 8,684,953 B2 | 4/2014 | Cabiri |
| 8,728,010 B2 | 5/2014 | Hirshman |
| 8,728,116 B1 | 5/2014 | Janardhan |
| 8,740,957 B2 | 6/2014 | Masotti |
| 8,795,202 B2 | 8/2014 | Northrop |
| 8,795,254 B2 | 8/2014 | Layman |
| 8,846,006 B2 | 9/2014 | Frank |
| 8,880,149 B2 | 11/2014 | Barbot |
| 8,932,270 B2 | 1/2015 | O'Day |
| 9,038,639 B2 | 5/2015 | Pfeffer |
| 9,072,874 B2 | 7/2015 | Northrop |
| 9,138,561 B2 | 9/2015 | Stenzel |
| 9,192,743 B2 | 11/2015 | Stenzel |
| 9,227,037 B2 | 1/2016 | Northrop |
| 9,326,757 B2 | 5/2016 | Ravikumar |
| 9,346,093 B2 | 5/2016 | Cacace |
| 9,375,195 B2 | 6/2016 | Kamen |
| 9,383,421 B2 | 7/2016 | Vij |
| 9,656,004 B2 | 5/2017 | Duering |
| 9,669,240 B2 | 6/2017 | Köhler |
| 9,687,681 B2 | 6/2017 | Kohler |
| 9,775,523 B2 | 10/2017 | Gregorich |
| 9,861,450 B2 | 1/2018 | Bolan |
| 10,010,723 B2 | 7/2018 | Koehler |
| 10,028,666 B2 | 7/2018 | Gregorich |
| 10,035,002 B2 | 7/2018 | Weiss |
| 10,065,023 B2 | 9/2018 | Sela |
| 10,172,537 B2 | 1/2019 | Pfeffer |
| 10,201,333 B2 | 2/2019 | Nock |
| 10,555,753 B2 | 2/2020 | Moberg |
| 10,555,756 B2 | 2/2020 | Krieger |
| 10,695,540 B2 | 6/2020 | Kocaturk |
| 10,814,044 B2 | 10/2020 | Duering |
| 10,835,710 B2 | 11/2020 | Lederman |
| 10,976,388 B2 | 4/2021 | Yang et al. |
| 11,034,580 B2 | 6/2021 | Ostrovska |
| 11,052,242 B1 | 7/2021 | Gore |
| 11,062,473 B2 | 7/2021 | Fine |
| 11,071,869 B2 | 7/2021 | Leigh |
| 11,090,033 B2 | 8/2021 | Rebellino |
| 11,090,130 B2 | 8/2021 | Nemanic |
| 11,097,017 B2 | 8/2021 | Preihs |
| 11,105,873 B2 | 8/2021 | Poole |
| 11,116,405 B2 | 9/2021 | Partanen |
| 11,142,826 B2 | 10/2021 | Han |
| 11,202,888 B2 | 12/2021 | Paul, Jr. |
| 11,219,761 B2 | 1/2022 | Verzal |
| 11,226,383 B2 | 1/2022 | Sengupta |
| 11,234,654 B2 | 2/2022 | Han |
| 11,241,296 B2 | 2/2022 | Bolan |
| 11,260,222 B2 | 3/2022 | Olsen |
| 11,266,326 B2 | 3/2022 | Dyer |
| 11,298,567 B2 | 4/2022 | Vahala |
| 11,304,683 B2 | 4/2022 | Mitra |
| 11,318,280 B2 | 5/2022 | Weiss |
| 11,737,851 B2 | 8/2023 | Paul |

| | | |
|---|---|---|
| 2002/0055449 A1 | 5/2002 | Porta |
| 2002/0058868 A1 | 5/2002 | Hoshino |
| 2002/0107446 A1 | 8/2002 | Rabiner |
| 2002/0151787 A1 | 10/2002 | Bjornerud |
| 2003/0055332 A1 | 3/2003 | Daum |
| 2003/0055449 A1 | 3/2003 | Lee |
| 2003/0060731 A1 | 3/2003 | Fleischhacker |
| 2003/0060842 A1 | 3/2003 | Chin |
| 2003/0069520 A1 | 4/2003 | Skujins |
| 2003/0069521 A1 | 4/2003 | Reynolds |
| 2003/0100828 A1 | 5/2003 | Engelhard |
| 2003/0100829 A1 | 5/2003 | Zhong et al. |
| 2003/0120148 A1 | 6/2003 | Pacetti |
| 2003/0135114 A1 | 7/2003 | Pacetti |
| 2003/0167052 A1 | 9/2003 | Lee |
| 2003/0187461 A1 | 10/2003 | Chin |
| 2003/0208142 A1 | 11/2003 | Boudewijn |
| 2004/0082946 A1 | 4/2004 | Malis |
| 2004/0082948 A1 | 4/2004 | Stewart |
| 2004/0097880 A1 | 5/2004 | Schur |
| 2004/0143180 A1 | 7/2004 | Zhong |
| 2004/0167428 A1 | 8/2004 | Quick et al. |
| 2004/0167437 A1 | 8/2004 | Sharrow |
| 2004/0167438 A1 | 8/2004 | Sharrow |
| 2004/0167439 A1 | 8/2004 | Sharrow |
| 2004/0167442 A1 | 8/2004 | Shireman et al. |
| 2004/0186377 A1 | 9/2004 | Zhong et al. |
| 2004/0193140 A1 | 9/2004 | Griffin |
| 2004/0199240 A1 | 10/2004 | Dorn |
| 2004/0200881 A1 | 10/2004 | Gandy |
| 2004/0254445 A1 | 12/2004 | Bittner |
| 2004/0254450 A1 | 12/2004 | Griffin |
| 2005/0021002 A1 | 1/2005 | Deckman |
| 2005/0054952 A1 | 3/2005 | Eskuri |
| 2005/0065437 A1 | 3/2005 | Weber |
| 2005/0070793 A1 | 3/2005 | Pacetti |
| 2005/0096665 A1 | 5/2005 | Reynolds |
| 2005/0119615 A1 | 6/2005 | Noriega |
| 2005/0125053 A1 | 6/2005 | Yachia |
| 2005/0143650 A1 | 6/2005 | Winkel |
| 2005/0148865 A1 | 7/2005 | Weber |
| 2005/0149009 A1 | 7/2005 | Wakikaido |
| 2005/0165301 A1 | 7/2005 | Smith et al. |
| 2005/0215874 A1 | 9/2005 | Wang |
| 2005/0240165 A1 | 10/2005 | Miki |
| 2005/0277829 A1 | 12/2005 | Tsonton |
| 2005/0283215 A1 | 12/2005 | Desinger et al. |
| 2006/0004346 A1 | 1/2006 | Begg |
| 2006/0073101 A1 | 4/2006 | Oldfield |
| 2006/0100687 A1 | 5/2006 | Fahey |
| 2006/0122537 A1 | 6/2006 | Reynolds |
| 2006/0200048 A1 | 9/2006 | Furst |
| 2006/0253178 A1 | 11/2006 | Masotti |
| 2007/0016131 A1 | 1/2007 | Munger |
| 2007/0026555 A1 | 2/2007 | Lee |
| 2007/0043333 A1 | 2/2007 | Kampa et al. |
| 2007/0060878 A1 | 3/2007 | Bonnette |
| 2007/0083132 A1 | 4/2007 | Sharrow |
| 2007/0112331 A1 | 5/2007 | Weber |
| 2007/0135734 A1 | 6/2007 | Reynolds |
| 2007/0149037 A1 | 6/2007 | Souba |
| 2007/0162108 A1 | 7/2007 | Carlson |
| 2007/0208405 A1 | 9/2007 | Goodin |
| 2007/0244414 A1 | 10/2007 | Reynolds |
| 2007/0265551 A1 | 11/2007 | Pfister |
| 2007/0280850 A1 | 12/2007 | Carlson |
| 2008/0004689 A1 | 1/2008 | Jahnke |
| 2008/0021313 A1 | 1/2008 | Eidenschink |
| 2008/0021347 A1 | 1/2008 | Jacobsen |
| 2008/0021400 A1 | 1/2008 | Jacobsen |
| 2008/0021401 A1 | 1/2008 | Jacobsen |
| 2008/0021402 A1 | 1/2008 | Jacobsen |
| 2008/0021403 A1 | 1/2008 | Jacobsen |
| 2008/0021405 A1 | 1/2008 | Jacobsen |
| 2008/0021406 A1 | 1/2008 | Jacobsen |
| 2008/0021407 A1 | 1/2008 | Jacobsen |
| 2008/0021408 A1 | 1/2008 | Jacobsen |
| 2008/0045908 A1 | 2/2008 | Gould |
| 2008/0077085 A1 | 3/2008 | Eidenschink |

(56)                References Cited

U.S. PATENT DOCUMENTS

| 2008/0086047 | A1 | 4/2008 | Mcdaniel |
| 2008/0097294 | A1 | 4/2008 | Prather |
| 2008/0097395 | A1 | 4/2008 | Adams |
| 2008/0097398 | A1 | 4/2008 | Mitelberg |
| 2008/0097404 | A1 | 4/2008 | Yribarren |
| 2008/0125674 | A1 | 5/2008 | Bilecen |
| 2008/0125766 | A1 | 5/2008 | Lubock |
| 2008/0139925 | A1 | 6/2008 | Lubock |
| 2008/0147001 | A1 | 6/2008 | Al-Marashi |
| 2008/0194994 | A1 | 8/2008 | Bown |
| 2008/0195194 | A1 | 8/2008 | Pacetti |
| 2008/0262474 | A1 | 10/2008 | Northrop |
| 2008/0269641 | A1* | 10/2008 | O'Shaughnessy .... A61M 25/09 |
| | | | 600/585 |
| 2008/0272774 | A1 | 11/2008 | Bieri |
| 2008/0294231 | A1 | 11/2008 | Aguilar |
| 2008/0312597 | A1 | 12/2008 | Uihlein |
| 2009/0036832 | A1 | 2/2009 | Skujins |
| 2009/0043228 | A1 | 2/2009 | Northrop |
| 2009/0043283 | A1 | 2/2009 | Turnlund |
| 2009/0043372 | A1 | 2/2009 | Northrop |
| 2009/0117711 | A1 | 5/2009 | Harle |
| 2009/0118675 | A1 | 5/2009 | Czyscon |
| 2009/0118704 | A1 | 5/2009 | Sharrow |
| 2009/0177040 | A1 | 7/2009 | Lyons |
| 2009/0177119 | A1 | 7/2009 | Heidner |
| 2009/0192584 | A1 | 7/2009 | Gerdts |
| 2009/0227901 | A1 | 9/2009 | Hofmann |
| 2009/0264731 | A1 | 10/2009 | Sugiura |
| 2009/0292225 | A1 | 11/2009 | Chen |
| 2010/0004562 | A1 | 1/2010 | Jalisi |
| 2010/0030072 | A1 | 2/2010 | Casanova |
| 2010/0036364 | A1 | 2/2010 | Wuebbeling |
| 2010/0063383 | A1* | 3/2010 | Anderson ......... A61M 25/0127 |
| | | | 604/103.1 |
| 2010/0063479 | A1 | 3/2010 | Merdan |
| 2010/0069882 | A1 | 3/2010 | Jennings |
| 2010/0087849 | A1 | 4/2010 | Griffin |
| 2010/0145308 | A1 | 6/2010 | Layman |
| 2010/0152612 | A1 | 6/2010 | Headley, Jr. |
| 2010/0185080 | A1 | 7/2010 | Myhr |
| 2010/0201361 | A1 | 8/2010 | Edelman |
| 2010/0207291 | A1 | 8/2010 | Eidenschink |
| 2010/0254897 | A1 | 10/2010 | Frank |
| 2010/0268325 | A1 | 10/2010 | Gregorich |
| 2011/0022069 | A1 | 1/2011 | Mitusina |
| 2011/0098554 | A1 | 4/2011 | Mardor |
| 2011/0160834 | A1 | 6/2011 | Aggerholm |
| 2011/0166439 | A1 | 7/2011 | Pfeffer |
| 2011/0251519 | A1 | 10/2011 | Romoscanu |
| 2011/0270169 | A1 | 11/2011 | Gardeski |
| 2011/0276034 | A1 | 11/2011 | Tomarelli |
| 2012/0035434 | A1 | 2/2012 | Ferren et al. |
| 2012/0053419 | A1 | 3/2012 | Bloom |
| 2012/0053572 | A1 | 3/2012 | Rusu |
| 2012/0078087 | A1 | 3/2012 | Curry |
| 2012/0083877 | A1 | 4/2012 | Nguyen et al. |
| 2012/0108881 | A1 | 5/2012 | Chi Sing |
| 2012/0157935 | A1 | 6/2012 | Martin |
| 2012/0232658 | A1 | 9/2012 | Morgenstern et al. |
| 2012/0265229 | A1 | 10/2012 | Rottenberg |
| 2012/0289776 | A1 | 11/2012 | Keast |
| 2013/0030362 | A1 | 1/2013 | Wright |
| 2013/0046285 | A1 | 2/2013 | Griffin |
| 2013/0072904 | A1 | 3/2013 | Musbach |
| 2013/0085444 | A1 | 4/2013 | Heinrich |
| 2013/0123692 | A1 | 5/2013 | Zhang |
| 2013/0123768 | A1 | 5/2013 | Harlan |
| 2013/0131496 | A1* | 5/2013 | Jenkins .................. A61B 5/283 |
| | | | 600/411 |
| 2013/0158478 | A1 | 6/2013 | Kaufmann |
| 2013/0165942 | A1 | 6/2013 | Tan-Malecki |
| 2013/0231586 | A1 | 9/2013 | Tsonton |
| 2013/0274591 | A1 | 10/2013 | Sonmez |
| 2013/0274618 | A1 | 10/2013 | Hou |
| 2013/0274711 | A1 | 10/2013 | O'Day |
| 2013/0296718 | A1 | 11/2013 | Ranganathan |
| 2013/0304035 | A1 | 11/2013 | Cabiri |
| 2013/0324837 | A1 | 12/2013 | Meyer |
| 2014/0005558 | A1 | 1/2014 | Gregorich |
| 2014/0005647 | A1 | 1/2014 | Shufffler |
| 2014/0031843 | A1 | 1/2014 | Rottenberg |
| 2014/0053940 | A1 | 2/2014 | Konstorum |
| 2014/0058275 | A1 | 2/2014 | Gregorich |
| 2014/0081134 | A1 | 3/2014 | Fortson |
| 2014/0081244 | A1 | 3/2014 | Voeller |
| 2014/0121590 | A1 | 5/2014 | Degen |
| 2014/0121642 | A1 | 5/2014 | Jordan |
| 2014/0180302 | A1 | 6/2014 | Vetter et al. |
| 2014/0243615 | A1 | 8/2014 | Schaeffer |
| 2014/0243742 | A1 | 8/2014 | Pacheco |
| 2014/0350414 | A1 | 11/2014 | Mcgowan |
| 2014/0378916 | A1 | 12/2014 | Simpson |
| 2015/0011834 | A1 | 1/2015 | Ayala |
| 2015/0051583 | A1 | 2/2015 | Horvath |
| 2015/0051696 | A1 | 2/2015 | Hou |
| 2015/0073391 | A1 | 3/2015 | Hutchins |
| 2015/0083284 | A1 | 3/2015 | Rawson |
| 2015/0105796 | A1 | 4/2015 | Grace |
| 2015/0148706 | A1 | 5/2015 | Abner |
| 2015/0151081 | A1 | 6/2015 | Keith |
| 2015/0182671 | A1 | 7/2015 | Düring |
| 2015/0190614 | A1 | 7/2015 | Uihlein |
| 2015/0209551 | A1 | 7/2015 | Burdette |
| 2015/0265167 | A1 | 9/2015 | Mcgowan |
| 2015/0335391 | A1 | 11/2015 | Linderman |
| 2015/0338477 | A1 | 11/2015 | Schmidt |
| 2015/0342580 | A1 | 12/2015 | Clancy |
| 2015/0351644 | A1 | 12/2015 | Lee |
| 2015/0374929 | A1 | 12/2015 | Hyde |
| 2016/0008584 | A1 | 1/2016 | Root |
| 2016/0033059 | A1 | 2/2016 | Fonte |
| 2016/0045190 | A1 | 2/2016 | Elfman |
| 2016/0051384 | A1 | 2/2016 | Patel |
| 2016/0051798 | A1 | 2/2016 | Weber |
| 2016/0082228 | A1 | 3/2016 | Sela |
| 2016/0089515 | A1 | 3/2016 | Hansen |
| 2016/0158509 | A1 | 6/2016 | Wedan |
| 2016/0317212 | A1 | 11/2016 | Ge |
| 2017/0055908 | A1 | 3/2017 | Radman |
| 2017/0106171 | A1 | 4/2017 | Flores |
| 2017/0143317 | A1 | 5/2017 | Hoffman |
| 2017/0165456 | A1 | 6/2017 | Tutungi |
| 2017/0202480 | A1 | 7/2017 | Kim |
| 2017/0232158 | A1 | 8/2017 | Düring |
| 2017/0239450 | A1 | 8/2017 | Kocaturk et al. |
| 2017/0291013 | A1 | 10/2017 | Pereira |
| 2017/0347913 | A1* | 12/2017 | Isaacson ........... A61M 25/0127 |
| 2017/0348509 | A1 | 12/2017 | Burkholz |
| 2018/0078742 | A1 | 3/2018 | Butler |
| 2018/0078743 | A1 | 3/2018 | Kubo |
| 2018/0085027 | A1 | 3/2018 | Kimmel |
| 2018/0085184 | A1 | 3/2018 | Bolan |
| 2018/0140801 | A1 | 5/2018 | Voss |
| 2018/0161121 | A1 | 6/2018 | Butler |
| 2018/0185618 | A1 | 7/2018 | Sweeney |
| 2018/0193606 | A1 | 7/2018 | Patel |
| 2018/0193608 | A1 | 7/2018 | Thuren |
| 2018/0243530 | A1 | 8/2018 | Lederman |
| 2018/0289388 | A1 | 10/2018 | Lenker |
| 2018/0303603 | A1 | 10/2018 | Melsheimer |
| 2019/0046684 | A1 | 2/2019 | Roth |
| 2019/0083071 | A1 | 3/2019 | Rebellino |
| 2019/0167952 | A1 | 6/2019 | Paul, Jr. et al. |
| 2019/0192124 | A1 | 6/2019 | Park |
| 2019/0223975 | A1 | 7/2019 | Agostinelli et al. |
| 2019/0351182 | A1 | 11/2019 | Chou |
| 2019/0374279 | A1 | 12/2019 | Weitzner |
| 2020/0000545 | A1* | 1/2020 | Paul ................. A61B 17/00234 |
| 2020/0008678 | A1 | 1/2020 | Barbagli et al. |
| 2020/0069927 | A1 | 3/2020 | Malek |
| 2020/0121415 | A1 | 4/2020 | Mayes et al. |
| 2021/0077077 | A1 | 3/2021 | Mitra et al. |
| 2021/0106791 | A1 | 4/2021 | Uihlein |

(56) References Cited

U.S. PATENT DOCUMENTS

| | | |
|---|---|---|
| 2021/0177510 A1 | 6/2021 | Papaioannou |
| 2021/0178121 A1 | 6/2021 | Burdette |
| 2021/0187253 A1 | 6/2021 | Borm |
| 2021/0208225 A1 | 7/2021 | Gilbo |
| 2021/0220624 A1 | 7/2021 | Blacker |
| 2021/0228841 A1 | 7/2021 | Falb |
| 2021/0236017 A1 | 8/2021 | Pfeffer |
| 2021/0247472 A1 | 8/2021 | Kocaturk et al. |
| 2021/0251696 A1 | 8/2021 | Jochen |
| 2021/0255261 A1 | 8/2021 | Piferi |
| 2021/0267696 A1 | 9/2021 | Degertekin |
| 2021/0275155 A1 | 9/2021 | Hautvast |
| 2021/0282866 A1 | 9/2021 | Kamal |
| 2021/0295985 A1 | 9/2021 | Prokle |
| 2022/0015636 A1 | 1/2022 | Mak |
| 2022/0050154 A1 | 2/2022 | Schneider |
| 2022/0088353 A1 | 3/2022 | Paul, Jr. |
| 2022/0096116 A1 | 3/2022 | McFarland et al. |
| 2022/0101576 A1 | 3/2022 | Kaushik |
| 2022/0104913 A1 | 4/2022 | Blair |
| 2022/0218881 A1 | 7/2022 | Cook |
| 2023/0248241 A1 | 8/2023 | Anttila et al. |

FOREIGN PATENT DOCUMENTS

| | | |
|---|---|---|
| AU | 2002358281 | 7/2003 |
| CA | 2094250 A1 | 6/1992 |
| CA | 2462335 | 4/2003 |
| CN | 2930741 | 8/2007 |
| CN | 106943218 | 7/2017 |
| CN | 112426611 A | 3/2021 |
| DE | 19843427 | 3/2000 |
| DE | 20019484 | 5/2001 |
| DE | 10029738 | 1/2002 |
| DE | 20017836 | 2/2002 |
| DE | 10243261 | 3/2004 |
| DE | 60208057 | 6/2006 |
| DE | 102005022688 | 11/2006 |
| DE | 102005030472 | 1/2007 |
| DE | 202010004107 U1 | 6/2010 |
| DE | 202010016473 | 2/2012 |
| DE | 102011101680 | 9/2012 |
| DE | 102011081445 | 2/2013 |
| EP | 0315290 | 5/1989 |
| EP | 0561903 | 9/1993 |
| EP | 0628288 | 12/1994 |
| EP | 0561903 B1 | 7/1995 |
| EP | 0744186 | 11/1996 |
| EP | 0775500 | 5/1997 |
| EP | 0937481 | 8/1999 |
| EP | 0628288 B1 | 4/2000 |
| EP | 1011491 | 6/2000 |
| EP | 1116476 | 7/2001 |
| EP | 1116476 A2 | 7/2001 |
| EP | 1242138 | 9/2002 |
| EP | 1432467 | 6/2004 |
| EP | 1551490 | 7/2005 |
| EP | 1596894 | 11/2005 |
| EP | 1656963 A1 | 5/2006 |
| EP | 1819374 | 8/2007 |
| EP | 2228094 A1 | 9/2010 |
| EP | 2364746 | 9/2011 |
| EP | 2508213 A1 | 10/2012 |
| EP | 2675353 | 12/2013 |
| EP | 2762189 A1 | 8/2014 |
| EP | 3093037 | 11/2016 |
| EP | 2508213 B1 | 3/2018 |
| EP | 3288629 | 3/2018 |
| EP | 3349650 | 7/2018 |
| EP | 3586763 A2 | 1/2020 |
| EP | 3586763 A3 | 3/2020 |
| EP | 4008388 | 6/2022 |
| JP | 6032553 | 7/1985 |
| JP | H10248853 | 9/1998 |
| JP | H10290839 | 11/1998 |
| JP | H10314137 | 12/1998 |
| JP | H11285533 | 10/1999 |
| JP | 2005528126 | 9/2005 |
| JP | 2005334645 | 12/2005 |
| JP | 2006501974 | 1/2006 |
| JP | 2006520645 | 9/2006 |
| JP | 3962724 | 8/2007 |
| JP | 2008515563 | 5/2008 |
| JP | 2008272464 | 11/2008 |
| JP | 2009512475 | 3/2009 |
| JP | 2009183765 | 8/2009 |
| JP | 2010517722 | 5/2010 |
| JP | 4494782 | 6/2010 |
| JP | 2020022737 X | 2/2020 |
| NL | 1006612 | 1/1999 |
| WO | 9011313 | 10/1990 |
| WO | 9842268 | 10/1998 |
| WO | 9855016 | 12/1998 |
| WO | 0007652 | 2/2000 |
| WO | 20000064003 | 10/2000 |
| WO | 01045786 | 6/2001 |
| WO | 0195794 | 12/2001 |
| WO | 2002055146 | 7/2002 |
| WO | 03003982 | 1/2003 |
| WO | 03030982 | 4/2003 |
| WO | 03057302 | 7/2003 |
| WO | 2003057302 | 7/2003 |
| WO | 03092791 | 11/2003 |
| WO | 2004075941 | 9/2004 |
| WO | 2005112778 | 12/2005 |
| WO | 2006036786 | 4/2006 |
| WO | 2006063106 | 6/2006 |
| WO | 2006116538 A2 | 11/2006 |
| WO | 2006119645 A1 | 11/2006 |
| WO | 2007045913 | 4/2007 |
| WO | 2011008538 | 1/2011 |
| WO | 2012032881 | 3/2012 |
| WO | 2012112829 | 8/2012 |
| WO | 2016064753 A1 | 4/2016 |
| WO | 2016175882 | 11/2016 |
| WO | 2016176393 | 11/2016 |
| WO | 2017048759 | 3/2017 |
| WO | 2018182701 | 10/2018 |
| WO | 2018182701 A1 | 10/2018 |
| WO | 2021081079 | 4/2021 |

OTHER PUBLICATIONS

Basar et al., "Susceptibility artifacts from metallic markers and cardiac catheterization devices on a high-performance 0.55 T MRI system", Magnetic Resonance Imaging, (2021), vol. 77, pp. 14-20.
International Search Report and Written Opinion, Application No. PCT/US2023/030307, dated Dec. 18, 2023.
Nour et al., "Magnetic Resonance Image-Guided Focal Prostate Ablation", Seminars In Interventional Radiology, (2016), vol. 33, No. 3, pp. 206-216.
Yun et al., "Breast Magnetic Resonance Imaging-Guided Biopsy", The Korean Society of Radiology, (2016), 74(6), pp. 351-360.
U.S. Office Action (Non-Final Rejection) for U.S. Appl. No. 17/573,189, dated May 14, 2025.
U.S. Office Action (Notice of Allowance and Fees Due (PTOL-85)) for U.S. Appl. No. 17/573,073, dated Jun. 10, 2025 .
U.S. Office Action (Final Rejection) for U.S. Appl. No. 18/106,601, dated Jun. 2, 2025 .
U.S. Office Action (Non-Final Rejection) for U.S. Appl. No. 17/573,087, dated Apr. 22, 2025.
European Patent Office "Communication pursuant to Article 94(3)", App.ication No. 23 718 542.6, dated May 16, 2025.
Japanese Notification of Reason for Rejection, Application No. 2023-139741, mailed Jan. 8, 2025.
U.S. Office Action (Non-Final rejection) U.S. Appl. No. 18/836,215, dated Jul. 24, 2025.
U.S. Office Action (Non-Final) U.S. Appl. No. 18/238,747, dated Mar. 14, 2025.
Konings et al., "Heating around intravascular guidewires by resonating RF waves", Journal of Magnetic Resonance Imaging, 2000, vol. 12, pp. 79-85.

(56) References Cited

OTHER PUBLICATIONS

Ladd et al., "Reduction of resonant RF heating in intravascular catheters using coaxial chokes", Magnetic Resonance in Medicine: An Official Journal of the International Society for Magnetic Resonance in Medicine, 2000, vol. 43, No. 4, pp. 615-619.

Dempsey et al., "Investigation of the factors responsible for burns during MRI", Journal of Magnetic Resonance Imaging: An Official Journal of the International Society for Magnetic Resonance in Medicine, 2001, vol. 13, No. 4, pp. 627-631.

Nitz et al., "On the heating of linear conductive structures as guide wires and catheters in interventional MRI", Journal of Magnetic Resonance Imaging, 2001, vol. 13, No. 1, pp. 105-114.

Yeung et al., "RF safety of wires in interventional MRI: using a safety index", Magnetic Resonance in Medicine: An Official Journal of the International Society for Magnetic Resonance in Medicine, 2002, vol. 47, No. 1, pp. 187-193.

Dempsey et al., "MRI safety review", In Seminars in Ultrasound, CT and MRI, 2002, vol. 23, No. 5, pp. 392-401. Abstract Only.

Pictet et al., "Radiofrequency heating effects around resonant lengths of wire in MRI", Physics in Medicine & Biology, 2002, vol. 47 No. 16, 2973-2985. Abstract Only.

Yeung et al., "Minimizing RF heating of conducting wires in MRI", Magnetic Resonance in Medicine: An Official Journal of the International Society for Magnetic Resonance in Medicine, 2007, vol. 58 No. 5, pp. 1028-1034.

Martin et al., "MR imaging during endovascular procedures: an evaluation of the potential for catheter heating," Magnetic Resonance in Medicine: An Official Journal of the International Society for Magnetic Resonance in Medicine, 2009, vol. 61, No. 1, pp. 45-53.

Tong et al., "Practical aspects of MR imaging in the presence of conductive guide wires", Physics in Medicine & Biology, 2009, vol. 55 No. 1, Abstract Only.

Etezadi-Amoli et al., "Controlling radiofrequency-induced currents in guidewires using parallel transmit", Magnetic resonance in medicine, 2015, vol. 74, No. 6, pp. 1790-1802.

Campbell-Washburn et al., "Opportunities in interventional and diagnostic imaging by using high-performance low-field-strength MRI", Radiology, 2019, vol. 293, No. 2, pp. 384-393.

HiWire, Nitinol Core Wire Guide: Data Sheet, "Gain ureteral access with control", Cook 2013, URO-BM-HWDS-EN-201312.

Nano4Imaging, Your Health-Our Vision, MR wire guidewire: Technical Specification, Retrieved from Internet on Sep. 6, 2023. Retrieved from URL: https://www.nano4imaging.com/#EmeryGlide.

Basar et al., "Segmented nitinol guidewires with stiffness-matched connectors for cardiovascular magnetic resonance catheterization: preserved mechanical performance and freedom from heating", J. Cardiovascular Magnetic Resonance (2015), pp. 1-9.

Carpenter Corporation. "Magnetic Properties of Stainless Steels," pp. 1-9. Retrieved from Internet May 3, 2018.

European Communication Examination Report, Application No. 17178169.3, dated Aug. 7, 2019.

European Communication pursuant to Article 94 (3) EPC, Application No. 18829568.7, dated Jan. 30, 2024.

European Communication pursuant to Article 94 (3) EPC, Application No. 18829568.7, dated Mar. 24, 2022.

European Communication pursuant to Article 94(3) EPC, Application No. 19183472.0, dated Nov. 11, 2021.

European Communication pursuant to Article 96(2) EPC, Applcation No. 01942159.3, dated Jun. 14, 2006.

European Communication pursuant to Rule 161(1) and 162 EPC, Application No. 23713226.1, dated Sep. 17, 2024.

European extended Search report, Application No. 22150984.7, dated Dec. 5, 2022.

European extended Search Report, Application No. 17178169, dated Nov. 13, 2017.

European extended Search Report, Application No. 19183472.0, dated Feb. 13, 2020.

European Partial Search Report, Application No. 19183472.0, mailed Nov. 6, 2019.

European Partial Search Report, Application No. 22150984.7, dated Aug. 26, 2022.

European Patent Office "Examination Report" for European application No. 17178169.3, dated Aug. 7, 2019.

European Patent Office. "Supplementary European Search Report" Application No. 01942159, completed Feb. 2, 2006.

European Supplementary Search Report, Application No. 01942159. 3, completed Feb. 10, 2006.

Fichtinger et al., "Transrectal Prostate Biopsy Inside Closed MRI Scanner with Remote Actuation, under Real-Time Image Guidance", MICCAI, (2002), 5th International Conference, Tokyo, Japan, pp. 91-98.

Google Patents Translation of Chinese Application No. CN106943218A, retreived from the Internet, May 23, 2024.

Japanese 1st Office Action, Application No. 2019-121677, dated Apr. 18, 2023.

Japanese Office Action, Application No. 2023139741, dated May 7, 2024.

Kivelitz et al., "A Vascular Stent as an Active Component for Locally Enhanced Magnetic Resonance Imaging: Initial in Vivo Imaging Results After Catheter-guided Placements in Rabbits", Investigative Radiology, (2003), vol. 38, No. 3, pp. 147-152.

Kivelitz et al., "The Active Magnetic Resonance Imaging Stent (AMRIS): Initial Experimental In Vivo Results with Locally Amplified MR Angiography and Flow Measurements", (2001), Investigative Radiology, vol. 36, No. 11, pp. 625-631.

Kuehne Titus et al, "Pair of resonant fiducial markers for localization of endovascular catheters at all catheter orientations", Journal of Magnetic Resonance Imaging, Society for Magnetic Resonance Imaging, Oak Brook, IL, US, (2011), vol. 17, No. 5, doi: 10.1002/ JMRI. 10307, ISSN 1053-1807, pp. 620-624.

PCT International Search Report and Written Opinion, Application No. PCT/US2016/029661, dated Jul. 27, 2016.

PCT International Search Report and Written Opinion, Application No. PCT/US2018/063562, mailed Sep. 26, 2019.

PCT International Search Report and Written Opinion, Application No. PCT/US2023/062094, dated May 9, 2023.

PCT International Search Report and Written Opinion, Application No. PCT/US2023/062097, dated Jul. 13, 2023.

PCT International Search Report and Written Opinion, Application No. PCT/US2023/062104, dated Jun. 14, 2023.

PCT International Search Report, Application No. PCT/US2016/ 029670, dated Jul. 15, 2016.

US Office Action (Ex Parte Quayle) U.S. Appl. No. 16/454,905, dated Mar. 2, 2023.

US Office Action (Final Rejection) U.S. Appl. No. 17/573,073, dated Jul. 22, 2024.

US Office Action (Final), U.S. Appl. No. 17/573,104, dated May 30, 2024.

US Office Action (Final), U.S. Appl. No. 17/573,189, dated Dec. 19, 2024.

US Office Action (Non-Final Rejection) U.S. Appl. No. 17/573,073, dated Jan. 31, 2024.

US Office Action (Non-Final Rejection) U.S. Appl. No. 18/106,601, dated Nov. 18, 2024.

US Office Action (Non-Final Rejection), for U.S. Appl. No. 17/573,073, dated Dec. 17, 2024.

US Office Action (Non-Final) U.S. Appl. No. 16/454,905, dated Oct. 13, 2022.

US Office Action (Non-Final), U.S. Appl. No. 16/207,391, dated Feb. 19, 2021.

US Office Action (Non-Final), U.S. Appl. No. 17/539,683, dated Dec. 8, 2022.

US Office Action (Non-Final), U.S. Appl. No. 17/573,104, dated Dec. 22, 2023.

US Office Action (Non-Final), U.S. Appl. No. 17/573,189, dated Jun. 24, 2024.

US Office Action (Non-Final), U.S. Appl. No. 18/233,519, dated Mar. 5, 2024.

US Office Action (Notice of Allowance), U.S. Appl. No. 17/539,683, dated Mar. 31, 2023.

(56) References Cited

OTHER PUBLICATIONS

Weitschies et al., "Magnetic Markers as a Noninvasive Tool to Monitor Gastrointestinal Transit", IEEE, Transactions on Biomedical Engineering, (1994), vol. 41, No. 2, doi:10.1109/10.284931, ISSN 0018-9294, pp. 192-195.

Japanese Notification of Refusal, Application No. 2022002110, dated Oct. 8, 2025.

US Office Action (Non-Final Rejection) for U.S. Appl. No. 18/923,852, mailed Nov. 3, 2025.

European Communication pursuant to Article 94(3), Application No. 23718542.6, dated Dec. 9, 2025.

U.S. Office Action (Final Rejection) for U.S. Appl. No. 18/238,747, dated Dec. 16, 2025.

U.S. Office Action (Non-Final Rejection) for U.S. Appl. No. 19/027,914, dated Dec. 18, 2025.

U.S. Office Action (Non-Final Rejection) for U.S. Appl. No. 17/573,073, mailed Dec. 3, 2025.

U.S. Office Action (Final Rejection) for U.S. Appl. No. 18/836,215 dated Jan. 2, 2026.

U.S. Office Action (Non-Final Rejection) for U.S. Appl. No. 18/106,601, dated Jan. 9, 2026.

Cross et al., "Nitinol Characterization Study," Issued by Originator as Report No. GER-14188, (1969), NASA CR-1433, pp. 1-60.

European extended search report, Application No. 25196868.1, dated Jan. 21, 2026.

* cited by examiner

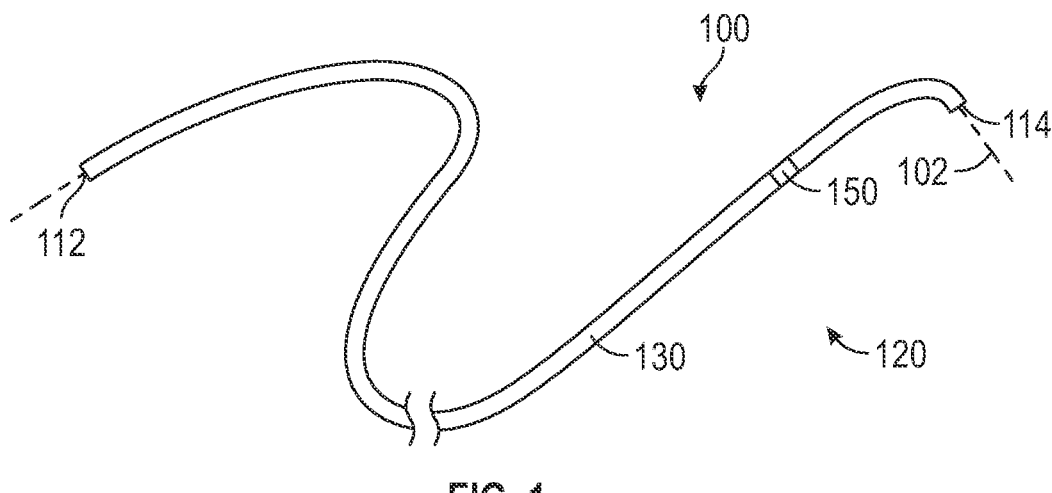
FIG. 1
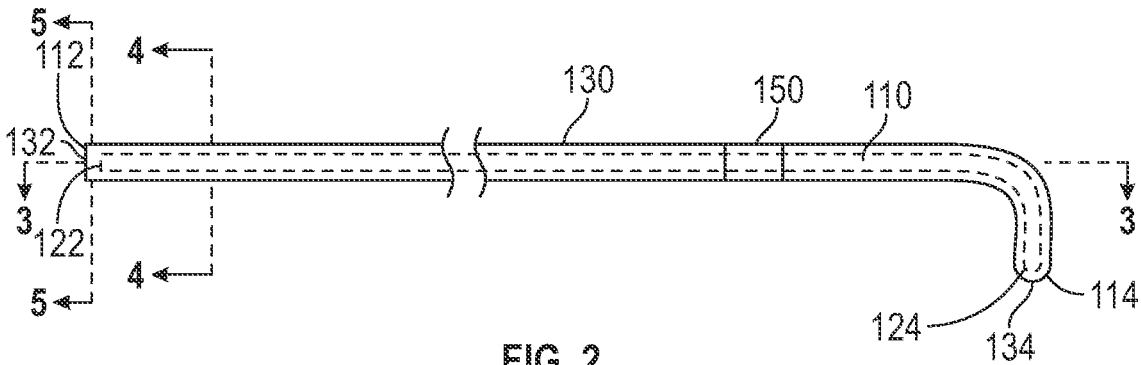
FIG. 2
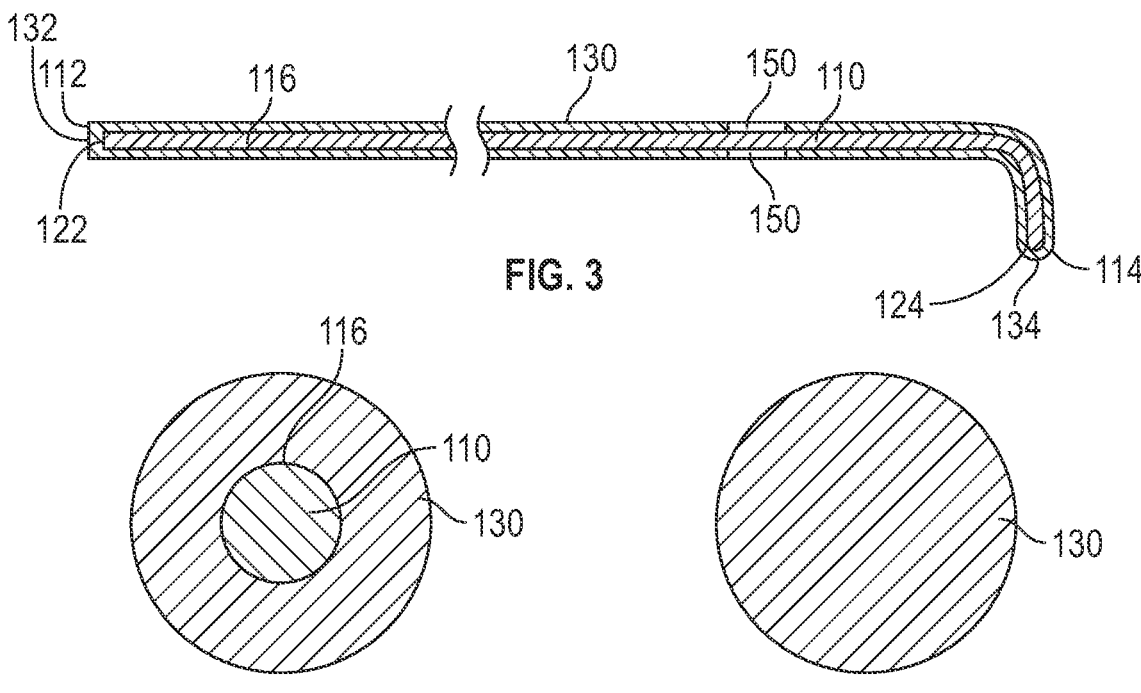
FIG. 3
FIG. 4
FIG. 5

600

Placing portion of
patient within MRI
system ——— 610

Grasping wireguide ——— 612

Inserting distal end of
wireguide into body
vessel ——— 614

Advancing distal end of
wire guide through body
vessel ——— 616

Operating scanner of
MRI system to scan
portion of patient ——— 618

Obtaining magnetic
resonance image ——— 620

Withdrawing wireguide
from body vessel ——— 622

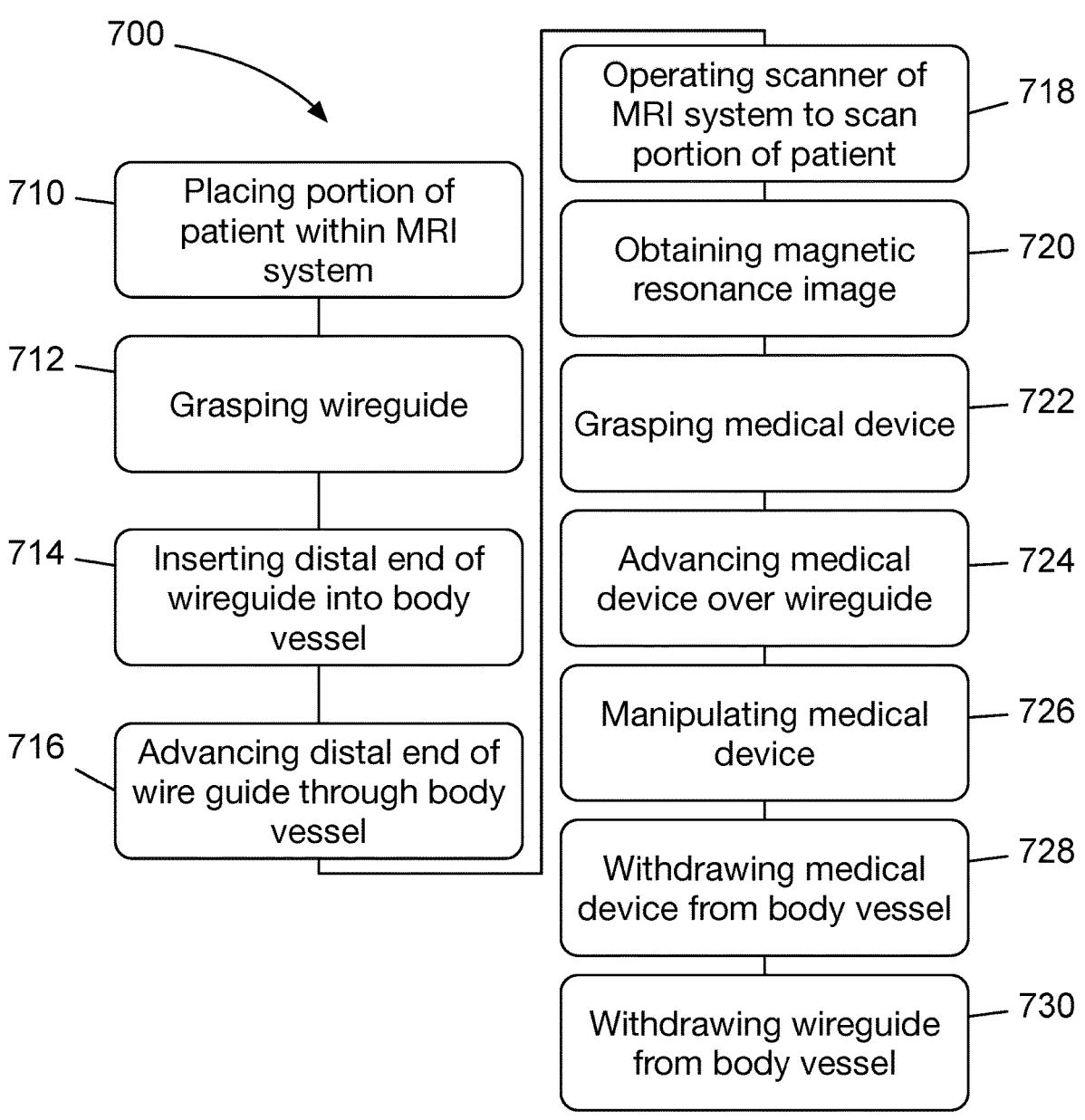

700

710 — Placing portion of patient within MRI system

712 — Grasping wireguide

714 — Inserting distal end of wireguide into body vessel

716 — Advancing distal end of wire guide through body vessel

Operating scanner of MRI system to scan portion of patient — 718

Obtaining magnetic resonance image — 720

Grasping medical device — 722

Advancing medical device over wireguide — 724

Manipulating medical device — 726

Withdrawing medical device from body vessel — 728

Withdrawing wireguide from body vessel — 730

FIG. 11

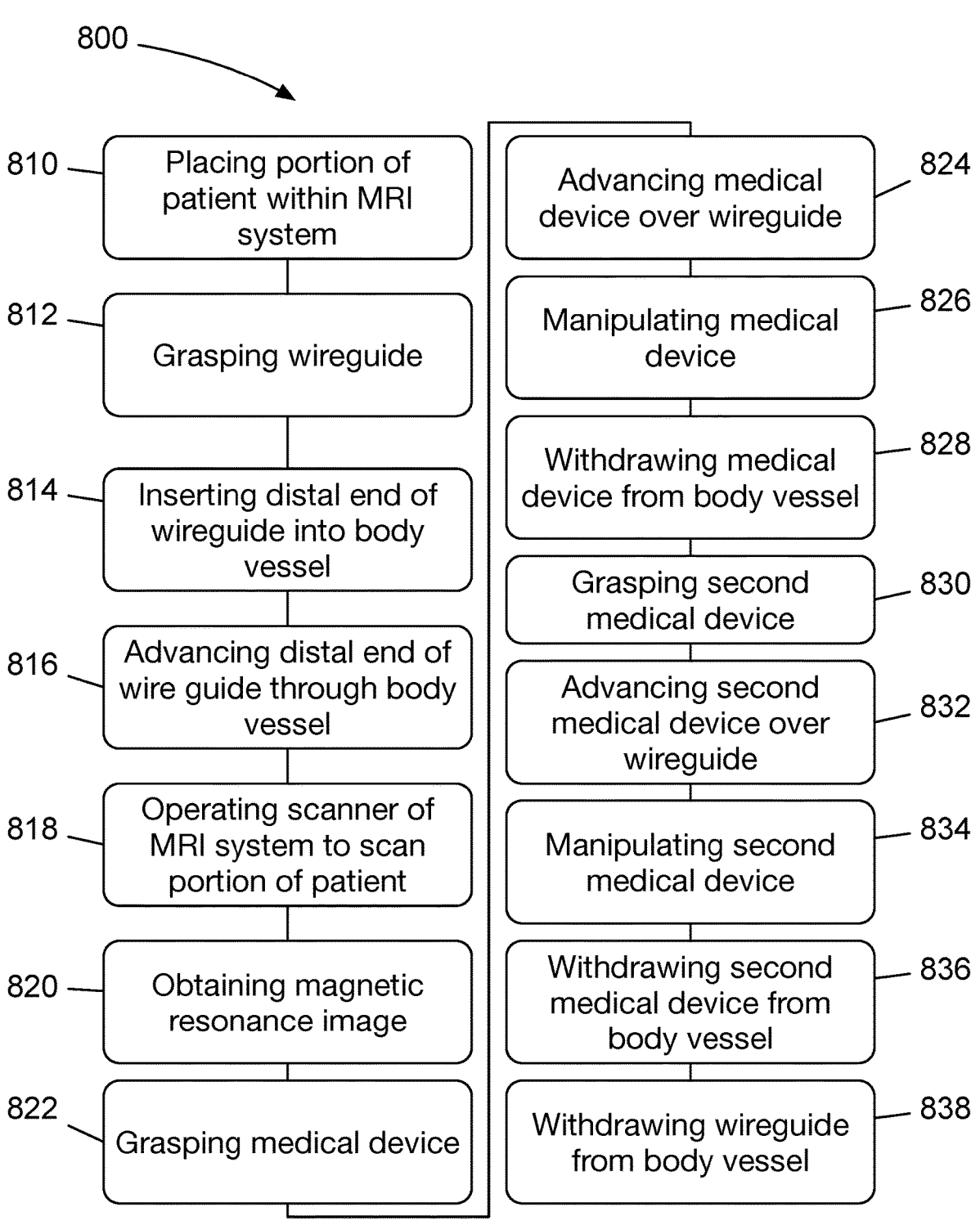

800

810 — Placing portion of patient within MRI system

812 — Grasping wireguide

814 — Inserting distal end of wireguide into body vessel

816 — Advancing distal end of wire guide through body vessel

818 — Operating scanner of MRI system to scan portion of patient

820 — Obtaining magnetic resonance image

822 — Grasping medical device

Advancing medical device over wireguide — 824

Manipulating medical device — 826

Withdrawing medical device from body vessel — 828

Grasping second medical device — 830

Advancing second medical device over wireguide — 832

Manipulating second medical device — 834

Withdrawing second medical device from body vessel — 836

Withdrawing wireguide from body vessel — 838

Forming a continuous core member of a metallic material — 910

Disposing jacket on continuous core member — 912

Evaluating jacket — 914

Transferring wireguide to intended user — 916

1000

Forming a plurality of continuous core members —— 1010

Disposing jacket on each continuous core member —— 1012

Evaluating each jacket —— 1014

Destroying any wireguide without full encapsulation —— 1016

Transferring first wireguide to first intended user —— 1018

Transferring second wireguide to second intended user —— 1020

| Description | Batch # | Scan # | Scan Time (min) | Whole Phantom Average SAR (W/kg) | Maximum Temperature Rise (°C) (Probe #) | | | |
|---|---|---|---|---|---|---|---|---|
| | | | | | 1 | 2 | 3 | 4 |
| Cook Medical Hi Wire | 0884 | 1 | 7:30 | 1.04 | 1.75 | 0.79 | 0.63 | 1.61 |
| | | 2 | 5:44 | 0.92 | 2.13 | 0.88 | 0.61 | 1.72 |
| | | 3 | 2:03 | 1.09 | 1.68 | 0.56 | 0.30 | 1.60 |
| | | 4 | 2:03 | 1.09 | 27.29 | 1.75 | 0.41 | 3.18 |
| Cook Medical Segmented Wire | 0885 | 5 | 2:03 | 1.09 | 0.27 | 0.52 | 0.37 | 0.42 |
| | | 6 | 7:30 | 1.04 | 0.61 | 0.85 | 0.63 | 0.39 |
| | | 7 | 2:03 | 1.09 | 2.54 | 0.71 | 0.44 | 0.22 |
| | | 8 | 7:30 | 1.04 | 2.13 | 0.95 | 0.62 | 0.11 |

FIG. 16

| Covering Electrical Conductivity (S/m) | Covering Thickness (mm) | Normalized Heating |
|---|---|---|
| 1e-15 | 0.0625 | 0.27 |
| 1e-5 | 0.0625 | 0.27 |
| 0.001 | 0.0625 | 0.32 |
| 0.01 | 0.0625 | 0.63 |
| 0.5 | 0.0625 | 1.0 |
| No Covering (Bare Wire) | N/A | 1.0 |

FIG. 17

| Covering Thickness (mm) | Electrical Conductivity (S/m) | Normalized Heating |
|---|---|---|
| 0.250 | 1.0e-15 | 0.11 |
| 0.125 | 1.0e-15 | 0.15 |
| 0.0625 | 1.0e-15 | 0.27 |
| 0.030 | 1.0e-15 | 0.47 |
| No Covering (Bare Wire) | N/A | 1.0 |

FIG. 18

| Material | Electrical Conductivity (S/m) |
|---|---|
| Nylon | 1e-13 |
| PTFE | 1e-9 |
| Polypropylene | 1e-14 |
| Rubber | 1e-12 |

FIG. 19

$$\nabla \times \mu_r^{-1}(\nabla \times \boldsymbol{E}) - \omega^2 \varepsilon_0 \mu_0 \left( \varepsilon_r - \frac{j\sigma}{\omega\varepsilon_0} \right) \boldsymbol{E} = 0$$

FIG. 20

$$k \left( \frac{\partial^2 T}{\partial r^2} + \frac{\omega}{r}\frac{\partial T}{\partial r} \right) + \quad q \quad + \underbrace{\rho_{bl} w_{bl} c_{bl} \left( T_{bl,a} - T \right)}_{\text{Perfusion Term}} = \rho c \frac{\partial T}{\partial t}$$

FIG. 21

$$q = \boldsymbol{J} \quad \boldsymbol{E}$$

FIG. 22

MRI COMPATIBLE INTERVENTIONAL MEDICAL DEVICES AND RELATED METHODS

FIELD

The disclosure relates generally to the field of medical devices. More particularly, the disclosure relates to interventional medical devices, such as wire guides, useful in interventional procedures performed under magnetic resonance imaging (MRI), methods of imaging a portion of a body using MRI, methods of performing interventional medical treatment under MRI, and methods of making interventional medical devices.

BACKGROUND

Interventional procedures conducted under MRI have several benefits over X-Ray-guided interventions. For example, the patient is not exposed to ionizing radiation. Also, MRI provides the ability to characterize tissue and fluid flow during an interventional procedure. For at least these reasons, the use of interventional MRI is gaining wider acceptance and the number of procedures that can be performed under MRI is generally increasing.

The art provides only a limited number of interventional medical devices suitable for use under MRI, however, which continues to limit growth of the use of interventional MRI procedures. As a result, patients have not yet benefitted fully from interventional MRI technologies and, indeed, are often still limited to less convenient, and potentially less effective, options for certain treatments.

Wire guides are fundamental to the performance of interventional procedures, making the development of an MRI compatible wire guide a critical step in the wider adoption of interventional MRI procedures. To date, development of an MRI compatible wire guide has largely focused on relatively complicated segmented constructions and the use of non-metallic materials in an attempt to avoid the anticipated RF heating, deflection, and image artefacts believed to be associated with the use of devices having metal components under MRI. While the purpose-specific designs of segmented and non-metallic wire guides can indeed avoid RF heating, deflection, and artefacts, wire guides made in accordance with these designs have proven to have drawbacks, too. For example, segmented and non-metallic wire guides can have inadequate mechanical properties, trackability, and torqueability such that clinical adoption is limited despite the expected advantages provided by the MRI compatibility of such devices.

A need remains, therefore, for new and improved MRI compatible wire guides and related methods, including methods of imaging a portion of a body vessel using MRI, methods of performing interventional medical treatment under MRI, and methods of making interventional medical devices.

BRIEF SUMMARY OF SELECTED EXAMPLES

Various example interventional medical devices useful in interventional procedures performed under MRI are described.

An example wire guide comprises a continuous core member formed of a metallic material and having an outer surface; and a jacket disposed on the core member such that the outer surface of the core member is fully encapsulated by the jacket.

Another example wire guide comprises a continuous core member formed of a metallic material and having an outer surface, the core member having a first susceptibility; a marker disposed on the outer surface of the core member and formed of a second metallic material having a second susceptibility that is different from the first susceptibility; and a jacket disposed on the core member and the marker such that no portion of the outer surface of the core member is exposed to the external environment surrounding the wire guide.

Another example wire guide comprises a continuous core member formed of a metallic material and having an outer surface, the core member having a first susceptibility; a jacket disposed on the core member such that no portion of the outer surface of the core member is exposed to the external environment surrounding the wire guide; and a marker disposed within the thickness of the jacket and formed of a second metallic material having a second susceptibility that is different from the first susceptibility.

Various example methods of imaging a portion of a body vessel of a patient using MRI are described.

An example method of imaging a portion of a body vessel of a patient using MRI comprises placing a portion of a patient within or adjacent an MRI system having a scanner such that a portion of the body vessel is located within the area within which the magnetic field of the scanner of the MRI system will be present once the scanner of the system is activated; grasping a wire guide comprising a continuous core member and a continuous jacket disposed over the entire core member, the core member formed of a metallic material and having a first length and the jacket having a second length that is greater than the first length; inserting the distal end of the wire guide into the body vessel; advancing the distal end of the wire guide through the body vessel until the distal end of the wire guide is disposed at a first position within a first portion of the body vessel that is located within the scanner of the MRI system; operating the scanner of the MRI system to scan the portion of the patient that is positioned within the scanner and that includes the first portion of the body vessel; obtaining a magnetic resonance image of the first portion of the body vessel; and withdrawing the wire guide from the body vessel.

Another example method of imaging a portion of a body vessel of a patient using MRI comprises placing a portion of a patient within or adjacent an MRI system having a scanner such that a portion of the body vessel is located within the area within which the magnetic field of the scanner of the MRI system will be present once the scanner of the system is activated; grasping a wire guide comprising a continuous core member and a continuous jacket disposed over the entire core member, the core member formed of a metallic material and having a first length and the jacket having a second length that is greater than the first length; inserting the distal end of the wire guide into the body vessel; advancing the distal end of the wire guide through the body vessel until the distal end of the wire guide is disposed at a first position within a first portion of the body vessel that is located within the scanner of the MRI system; while advancing the distal end of the wire guide through the body vessel of the patient, operating the scanner of the MRI system to scan the portion of the patient that is positioned within the scanner and that includes the first portion of the body vessel and obtaining a magnetic resonance image of the first portion of the body vessel; and withdrawing the wire guide from the body vessel.

Another example method of imaging a portion of a body vessel of a patient using MRI comprises placing a portion of a patient within or adjacent an MRI system having a scanner such that a portion of the body vessel is located within the area within which the magnetic field of the scanner of the MRI system will be present once the scanner of the system is activated; grasping a wire guide comprising a continuous core member and a continuous jacket disposed over the entire core member, the core member formed of a metallic material and having a first length and the jacket having a second length that is greater than the first length; inserting the distal end of the wire guide into the body vessel; advancing the distal end of the wire guide through the body vessel until the distal end of the wire guide is disposed at a first position within a first portion of the body vessel that is located within the scanner of the MRI system; while advancing the distal end of the wire guide through the body vessel of the patient, repeatedly operating the scanner of the MRI system to scan the portion of the patient that is positioned within the scanner and that includes the first portion of the body vessel and repeatedly obtaining a magnetic resonance image of the first portion of the body vessel; and withdrawing the wire guide from the body vessel.

Various example methods of performing interventional medical treatment under MRI are also described.

An example method of performing interventional medical treatment under MRI comprises placing a portion of a patient within or adjacent an MRI system having a scanner such that a portion of the body vessel is located within the area within which the magnetic field of the scanner of the MRI system will be present once the scanner of the system is activated; grasping a wire guide having a wire guide proximal end and a wire guide distal end and comprising a continuous core member and a continuous jacket disposed over the entire core member, the core member formed of a metallic material and having a first length and the jacket having a second length that is greater than the first length; inserting the wire guide distal end into said body vessel; advancing the distal end of the wire guide through said body vessel until the distal end of the wire guide is disposed at a first position within a first portion of said body vessel that is located within the scanner of the MRI system; grasping a medical device having a medical device proximal end and a medical device distal end and comprising an elongate member defining a lumen; passing the medical device distal end over the wire guide proximal end to dispose the wire guide proximal end within the lumen of the elongate member of the medical device; advancing the medical device distal end over the wire guide and into said body vessel until the medical device distal end reaches said point of treatment within said body vessel; manipulating the medical device proximal end to produce a manipulation of the medical device distal end at the point of treatment; operating the scanner of the MRI system to scan the portion of the patient that is positioned within the scanner and that includes the first portion of the body vessel; obtaining a magnetic resonance image of the first portion of the body vessel; withdrawing the medical device from the body vessel; and withdrawing the wire guide from the body vessel.

Another example method of performing interventional medical treatment under MRI comprises placing a portion of a patient within or adjacent an MRI system having a scanner such that a portion of the body vessel is located within the area within which the magnetic field of the scanner of the MRI system will be present once the scanner of the system is activated; grasping a wire guide having a wire guide proximal end and a wire guide distal end and comprising a continuous core member and a continuous jacket disposed over the entire core member, the core member formed of a metallic material and having a first length and the jacket having a second length that is greater than the first length; inserting the wire guide distal end into said body vessel; advancing the distal end of the wire guide through said body vessel until the distal end of the wire guide is disposed at a first position within a first portion of said body vessel that is located within the scanner of the MRI system; grasping a medical device having a medical device proximal end and a medical device distal end and comprising an elongate member defining a lumen; passing the medical device distal end over the wire guide proximal end to dispose the wire guide proximal end within the lumen of the elongate member of the medical device; advancing the medical device distal end over the wire guide and into said body vessel until the medical device distal end reaches said point of treatment within said body vessel; manipulating the medical device proximal end to produce a manipulation of the medical device distal end at the point of treatment; while advancing the distal end of the wire guide through the body vessel of the patient, repeatedly operating the scanner of the MRI system to scan the portion of the patient that is positioned within the scanner and that includes the first portion of the body vessel and repeatedly obtaining a magnetic resonance image of the first portion of the body vessel; withdrawing the medical device from the body vessel; and withdrawing the wire guide from the body vessel.

Another example method of performing interventional medical treatment under MRI comprises placing a portion of a patient within or adjacent an MRI system having a scanner such that a portion of the body vessel is located within the area within which the magnetic field of the scanner of the MRI system will be present once the scanner of the system is activated; grasping a wire guide having a wire guide proximal end and a wire guide distal end and comprising a continuous core member and a continuous jacket disposed over the entire core member, the core member formed of a metallic material and having a first length and the jacket having a second length that is greater than the first length; inserting the wire guide distal end into said body vessel; advancing the distal end of the wire guide through said body vessel until the distal end of the wire guide is disposed at a first position within a first portion of said body vessel that is located within the scanner of the MRI system; grasping a medical device having a medical device proximal end and a medical device distal end and comprising an elongate member defining a lumen; passing the medical device distal end over the wire guide proximal end to dispose the wire guide proximal end within the lumen of the elongate member of the medical device; advancing the medical device distal end over the wire guide and into said body vessel until the medical device distal end reaches said point of treatment within the body vessel; manipulating the medical device proximal end to produce a manipulation of the medical device distal end at the point of treatment; while advancing the medical device distal end over the wire guide and into the body vessel, repeatedly operating the scanner of the MRI system to scan the portion of the patient that is positioned within the scanner and that includes the first portion of the body vessel and repeatedly obtaining a magnetic resonance image of the first portion of the body vessel; withdrawing the medical device from the body vessel; and withdrawing the wire guide from the body vessel.

Another example method of performing interventional medical treatment under MRI comprises placing a portion of a patient within or adjacent an MRI system having a scanner such that a portion of the body vessel is located within the area within which the magnetic field of the scanner of the MRI system will be present once the scanner of the system is activated; grasping a wire guide having a wire guide proximal end and a wire guide distal end and comprising a continuous core member and a continuous jacket disposed over the entire core member, the core member formed of a metallic material and having a first length and the jacket having a second length that is greater than the first length; inserting the wire guide distal end into said body vessel; advancing the distal end of the wire guide through said body vessel until the distal end of the wire guide is disposed at a first position within a first portion of said body vessel that is located within the scanner of the MRI system; grasping a medical device having a medical device proximal end and a medical device distal end and comprising an elongate member defining a lumen; passing the medical device distal end over the wire guide proximal end to dispose the wire guide proximal end within the lumen of the elongate member of the medical device; advancing the medical device distal end over the wire guide and into said body vessel until the medical device distal end reaches said point of treatment within the body vessel; manipulating the medical device proximal end to produce a manipulation of the medical device distal end at the point of treatment; while manipulating the medical device proximal end to produce a manipulation of the medical device distal end at the point of treatment, repeatedly operating the scanner of the MRI system to scan the portion of the patient that is positioned within the scanner and that includes the first portion of the body vessel and repeatedly obtaining a magnetic resonance image of the first portion of the body vessel; withdrawing the medical device from the body vessel; and withdrawing the wire guide from the body vessel.

Another example method of performing interventional medical treatment under MRI comprises placing a portion of a patient within or adjacent an MRI system having a scanner such that a portion of the body vessel is located within the area within which the magnetic field of the scanner of the MRI system will be present once the scanner of the system is activated; grasping a wire guide having a wire guide proximal end and a wire guide distal end and comprising a continuous core member and a continuous jacket disposed over the entire core member, the core member formed of a metallic material and having a first length and the jacket having a second length that is greater than the first length; inserting the wire guide distal end into said body vessel; advancing the distal end of the wire guide through said body vessel until the distal end of the wire guide is disposed at a first position within a first portion of said body vessel that is located within the scanner of the MRI system; grasping a medical device having a medical device proximal end and a medical device distal end and comprising an elongate member defining a lumen; passing the medical device distal end over the wire guide proximal end to dispose the wire guide proximal end within the lumen of the elongate member of the medical device; advancing the medical device distal end over the wire guide and into said body vessel until the medical device distal end reaches said point of treatment within the body vessel; manipulating the medical device proximal end to produce a manipulation of the medical device distal end at the point of treatment; while advancing the wire guide distal end through the body vessel, advancing the medical device distal end over the wire guide into the body vessel, and manipulating the medical device proximal end, repeatedly operating the scanner of the MRI system to scan the portion of the patient that is positioned within the scanner and that includes the first portion of the body vessel and repeatedly obtaining a magnetic resonance image of the first portion of the body vessel; withdrawing the medical device from the body vessel; and withdrawing the wire guide from the body vessel.

Various example methods of making wire guides are also described.

An example method of making a wire guide comprises forming a continuous core member of a metallic material, the continuous core member having an outer surface; and disposing a jacket on the continuous core member such that the outer surface of the core member is in continuous contact with the jacket and such that no portion of the outer surface of the core member is exposed to the external environment surrounding the wire guide.

Another example method of making a wire guide comprises forming a continuous core member formed of a metallic material and having an outer surface; disposing a jacket on the continuous core member such that the outer surface of the core member is in continuous contact with the jacket and such that no portion of the outer surface of the core member is exposed to the external environment surrounding the wire guide; evaluating the jacket to determine if the outer surface of the core member is in continuous contact with the jacket; and transferring the wire guide to an intended user of the wireguide only if the evaluating step results in a determination that the outer surface of the core member is in continuous contact with the jacket.

An example method of making a plurality of wire guides comprises forming a plurality of continuous core members, each continuous core member of the plurality of continuous core members formed of a metallic material and having an outer surface; disposing a jacket on the outer surface of each continuous core member such that the outer surface of each continuous core member is in continuous contact with the jacket and such that no portion of the outer surface of each continuous core member is exposed to the external environment surrounding the wire guide of the plurality of wire guides; evaluating each jacket to determine if the outer surface of each continuous core member is in continuous contact with the jacket disposed on the outer surface of the continuous core member. An optional step includes destroying any wire guides from the plurality of wire guides for which the evaluating step results in a determination that the outer surface of the continuous core member is not in continuous contact with the jacket disposed on the continuous core member.

Additional understanding of these and other example methods of imaging a portion of a body vessel using MRI, methods of performing interventional medical treatment under MRI, interventional medical devices, such as wire guides, useful in performing treatment under MRI, and methods of making interventional medical devices can be obtained by review of the detailed description of selected examples, below, and the references drawings.

DESCRIPTION OF FIGURES

FIG. 1 is a perspective view of an example interventional medical device.

FIG. 2 is a side view of the example interventional medical device illustrated in FIG. 1.

FIG. 3 is a lengthwise sectional view of the example interventional medical device illustrated in FIG. 1, taken along line 3-3 in FIG. 2.

FIG. 4 is a magnified sectional view of the interventional medical device illustrated in FIG. 1, taken along line 4-4 in FIG. 2.

FIG. 5 is a magnified sectional view of the interventional medical device illustrated in FIG. 1, taken along line 5-5 in FIG. 2.

FIG. 11 is a flowchart illustration of an example method of performing interventional medical treatment under MRI.

FIG. 12 is a flowchart illustration of another example method of performing interventional medical treatment under MRI.

FIG. 16 presents data referenced in an Example described herein in tabular format.

FIG. 17 presents data referenced in an Example described herein in tabular format.

FIG. 18 presents data referenced in an Example described herein in tabular format.

FIG. 19 presents data referenced in an Example described herein in tabular format.

FIG. 20 presents an equation referenced in an Example described herein.

FIG. 21 presents an equation referenced in an Example described herein.

FIG. 22 presents an equation referenced in an Example described herein.

DETAILED DESCRIPTION OF SELECTED EXAMPLES

Figure 6:
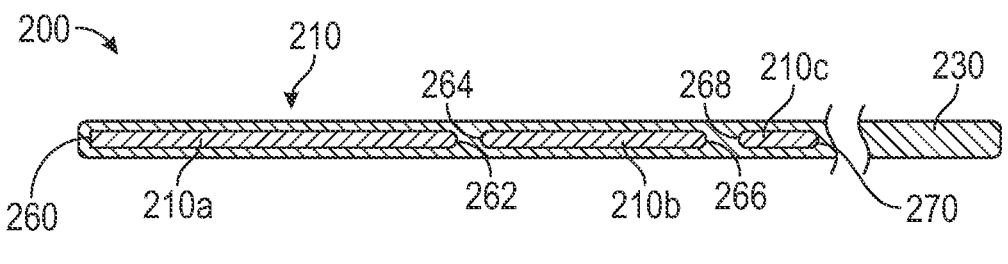
FIG. 6 is a lengthwise sectional view, partially broken away, of another example interventional medical device.

The following detailed description and the appended drawings describe and illustrate various example methods of imaging a portion of a body vessel using MRI, methods of performing interventional medical treatment under MRI, wire guides useful in performing interventional treatment under MRI, and methods of making wire guides. The description and illustration of these examples are provided to enable one skilled in the art to perform methods of imaging a portion of a body vessel using MRI, methods of performing interventional medical treatment under MRI, and methods of making interventional medical devices, and to make and use interventional medical devices, such as wire guides. The inclusion of detailed descriptions of these examples is not intended to limit the scope of the invention, or its protection, in any manner. The invention is capable of being practiced or carried out in various ways and the examples described and illustrated herein are not considered exhaustive.

As used herein, the term "attached" refers to one member being secured to another member such that the members do not completely separate from each other during use performed in accordance with the intended use of an item that includes the members in their attached form.

As used herein, the term "circumference" refers to an external enclosing boundary of a body, element, or feature and does not impart any structural configuration on the body, element, or feature.

As used herein, the term "continuous" refers to a structural configuration of an element in which the element extends from a first terminal end of the element to a second terminal end of the element in an uninterrupted manner such that no additional terminal ends exist between the first and second terminal ends. The term includes structural configurations in which two structural members, such as segments of the same or different materials, are joined end-to-end such that no internal terminal ends exist in the combined structure.

As used herein, the term "magnetic susceptibility" refers to the intrinsic property of a material that relates to how much the material will become magnetized in an applied magnetic field.

As used herein, the term "marker" refers to a discrete deposit of a first material on a second material such that the first material is visible under MRI and is distinguishable from the second material under MRI, a portion of an interventional device in which a first material has been incorporated into a second material such that the combination of the first and second materials is visible under MRI and is distinguishable from the second material under MRI, and a portion of an interventional device in which a material that forms a portion of an interventional device has been manipulated such that the portion is visible under MRI and is distinguishable from the remainder of the interventional device under MRI.

As used herein, the term "MRI system" refers to magnetic resonance equipment that includes a magnet and scanner and that is suitable for medical imaging purposes. The term includes MRI systems that define a bore within which a patient, or a portion of a patient, can be positioned, open MRI systems, and portable MRI systems that can be moved relative to a patient to position the patient, or a portion of the patient, relative to the scanner of the MRI system prior to initiation of an imaging procedure.

As used herein, the term "passive," in relation to a marker, refers to a marker that is either unpowered or powered exclusively by the electromagnetic field of a magnetic resonance scanner.

As used herein, the term "susceptibility," when not immediately preceded by "magnetic," refers to the ability of an element to influence an external magnetic field. Susceptibility is dependent on various properties of an element, including the size, density, geometric configuration, volume, and other physical properties of the element, and the magnetic susceptibility of the material of which the element is formed.

As used herein, the term "treatment" refers to a medical procedure performed on or in a portion of a body of a patient. Examples of treatments include delivery of an agent to a site within a body vessel, modification of a local environment inside of a body vessel such as by heating or cooling, and removal of a tissue or portion of a tissue from a site within a body of a patient (i.e., biopsy).

As used herein, the term "wire" and refers to a strand or rod of material. The term does not require any particular cross-sectional shape, composition, physical properties, or production method by which a referenced element was made.

FIGS. 1, 2, 3, 4, and 5 illustrate an example wire guide 100. The wire guide is an interventional medical device useful in interventional procedures performed under MRI. The wire guide 100 includes a core member 110 formed of a first material having a first susceptibility and a jacket 130 disposed on the core member 110. An optional marker 150 is attached to the core member 110 and, if included, is formed of a second material having a second susceptibility that is different from the first susceptibility. In embodiments in which a marker 150 is included, the first and second materials can be the same or different. Thus, the first and second materials can have the same or different magnetic susceptibility. If included, the marker 150 can be attached to the core member 110 in any suitable manner, such as with an adhesive, swaging, or other suitable forms of attaching one member to another. Also if included, the jacket 130 is advantageously disposed over the external surface of the marker 150 to provide a desirable fully encapsulated structure, as described above.

The core member 110 is a continuous elongate member having a proximal end 112, a distal end 114, a lengthwise axis 102 extending between the proximal end 112 and the distal end 114, and an axial length that extends from the proximal end 112 to the distal end 114. In this example, the core member 110 has an outer surface 116 that is in continuous contact with the jacket 130. Importantly, the entire outer surface 116 is fully encapsulated by the jacket 130. That is, no portion of the outer surface 116 of the core member 110 is exposed to the external environment surrounding the wire guide 110.

The core member 110 is formed of a metallic material, such as a metal or an alloy. The core member 110 can be formed of any suitable metallic material and selection of a suitable metallic material for a core member in a wire guide according to an embodiment can be based on various considerations, including any desired handling characteristics and any material selected for a marker, if included. Examples of metallic materials considered suitable for the core member include, but are not limited to, shape memory alloys, including nickel-titanium alloys such as Nitinol, Superelastic Nitinol SE508 straight with black oxide, matte finished Nitinol, polished Nitinol, nickel chromium, nickel cobalt, titanium, nickel oxide, cobalt chromium nickel molybdenum alloys, such as the alloy available under the trade name Elgiloy from Elgiloy Specialty Metals (Elgin, IL), combinations of those described herein, and any other metallic materials considered suitable for a particular embodiment.

As described in detail below, jacket 130 is a continuous jacket disposed over the entire length 104 of the core member 110. The continuous nature of the jacket 130 over the entire length 104 of the core member 110 is critical to the performance of the wire guide 100 according to this example as described herein. Core member 110 can include features that aid in the detection of disruptions in the continuous nature of the jacket 130, which may aid in assuring use of wire guides having a truly continuous jacket 130. For example, core member 110 can include a high contrast color jacket on its surface, disposed under jacket 130. The high contrast color of this underlayment jacket is relative to any color of jacket 130. For example, if jacket 130 is a dark color, such as a black or grey, a bright underlayment jacket, such as a yellow jacket, provides a high contrast color that, if visible upon inspection prior to use of a wire guide, can alert a user to a disruption in the continuous nature of jacket 130, allowing the user to assess whether the wire guide should be used in a contemplated procedure. Also, the core member 110 can include a coating that is responsive to exposure to an external substance other than the jacket 130, such as water. For example, the core member 110 can include a coating that changes color if it contacts an external substance, such as water. The color change can be visible under ambient light or another wavelength, such as under ultraviolet or another wavelength. Inspecting a wire guide or plurality of wire guides for suitable color changes, under appropriate light wavelengths, can be incorporated into methods of making a wire guide or a plurality of wire guide when the core member includes such a coating.

The core member 110 can have any suitable form and a skilled artisan will be able to select a suitable form for a wire guide according to a particular embodiment based on various considerations, including the intended use of the wire guide and the nature of any body vessel within which the wire guide is intended to be placed. In the illustrated example, the core member 110 is a wire having a substantially continuous outer diameter along its length 104. A core member having a taper along a length at its distal end is also considered suitable.

The core member 110 can have any suitable axial length and a skilled artisan will be able to select a suitable length for a core member in a wire guide according to a particular embodiment based on various considerations, including the intended use of the wire guide and the nature of any body vessel within which the wire guide is intended to be placed. Examples of lengths considered suitable for a core member in a wire guide according to the invention include, but are not limited to, lengths equal to, greater than, less than, or about 100 centimeters, 110 centimeters, 120 centimeters, 130 centimeters, 140 centimeters, 150 centimeters, 240 centimeters, 250 centimeters, 260 centimeters, 270 centimeters, 280 centimeters, between about 50 centimeters and about 350 centimeters, between about 100 centimeters and about 280 centimeters, between about 120 centimeters and about 260 centimeters, and any other length considered suitable for a wire guide according to a particular embodiment.

The jacket 130 is a continuous jacket disposed over the entire length 104 of the core member 110. As such, jacket fully encapsulates the core member 110. The jacket 130 has a proximal end 132, a distal end 134, and an axial length that extends from the proximal end 132 to the distal end 134. The length of the jacket 130 is greater than the length of the core member 110, ensuring that each of the terminal surface 122 of the proximal end 132 and the terminal surface 124 of the distal end 134 of the core member 110 are fully covered by the jacket 130.

The jacket is formed of one or more dielectric materials. In the illustrated embodiment, the jacket 130 is formed of a polymeric material. Any polymeric material that is a dielectric material can be used and a skilled artisan will be able to select a suitable polymeric material for the jacket in a wire guide according to a particular embodiment based on various considerations, including any desired handling and performance characteristics of the wire guide, such as torqueability and pushability. Examples of suitable polymeric materials include, but are not limited to, heat-formable polymeric materials, such as polyamide materials. These polymeric materials are considered desirable at least because of their ability to melt and flow between and around elements during a heat forming or heat shrinking process. Nylon is considered particularly advantageous at least because of its ready availability and well-characterized nature. Fluoropolymers, such as polytetrafluoroethylene, are also considered particularly advantageous as they have some of the highest characterized dielectric properties. Polyurethane and other polymeric materials are also considered advantageous. Additional jackets or other materials can be applied to the jacket 130 if desired. For example, a lubricious jacket can be applied as a topcoat on the jacket 130. The jacket 130 can have varying composition along the axial length of the wire guide 100. For example, a different polymer concentration can be used at one or both ends relative to a polymer concentration present in the jacket disposed over the axial midpoint of the wire guide. Polymer concentrations that provide a more rigid, durable, or both jacket can be used at one or both ends to provide resistance to tearing or other disruptions in the continuous nature of the jacket 130, which is critical to desirable performance of the wire guide 100.

In other embodiments, two or more dielectric materials can form the jacket. For example, a jacket having a first axial portion formed of a first polymer that is a dielectric material and a second axial portion formed of a second, different polymer that is a dielectric material can be used. Indeed, the two different polymers, while both providing the desired dielectric properties, can provide different properties, such as flexibility, hardness, and other properties. Furthermore, as described in more detail below, a jacket on a wire guide according to embodiments can comprise a first axial portion formed of a polymer that is a dielectric material and a second axial portion formed of a non-polymer that is a dielectric material, such as a ceramic or other nonpolymeric dielectric material.

The continuous nature of the jacket 130 over the entire length 104 of the core member 110 is critical to the performance of the wire guide 100 according to this example as described herein. As such, jacket 130 can include elements that resist formation of disruptions in the continuous nature of the jacket 130, such as fibers and other additives. Also, jacket 130 can be treated in a manner during manufacturing of the wire guide that renders jacket 130 relatively more resistant to such disruptions than if such treatment had not been performed. For example, jacket 130 can be subjected to electron beam irradiation, gamma irradiation, or other suitable treatments to cross-link the polymer of the jacket 130 to render jacket 130 more resistant to disruptions in the continuous nature of the jacket 130.

Wire guide 100 can include one or more markers 150. If included, the marker 150 can be disposed directly on the core member 110 such that the jacket 130 is disposed over the marker 150 and the core member 110. Alternatively, an included marker can be structurally positioned on the wire guide 100 in a manner such that the marker 150 has no direct structural contact with the core member 110. In the example wire guide 100 illustrated in FIGS. 4 through 8, the marker 150 is disposed directly on the core member such that no portion of jacket 130 is positioned between the marker 150 and the core member 110. As an alternative, a marker can be disposed within the thickness of the jacket such that a portion of the jacket is disposed between the inner surface of the marker and the external surface of the core member. In these embodiments, the marker is not in direct contact with the core member. If included, marker 150 is a passive marker and is formed of a metal or an alloy and has a susceptibility that is different from the susceptibility of the core member 110. Also alternatively, an outer surface of the jacket and an outer surface of one or more markers included in a wire guide according to an embodiment can be continuous with each other, such that the core member is fully encapsulated by the combination of the jacket and one or more markers. In these embodiments, the outer surface of the jacket and the outer surface of the one or more markers are advantageously flush with each other. Also alternatively, a marker can be disposed on a previously placed jacket. Marker 150 can have any structural configuration, and a skilled artisan will be able to select a suitable structural configuration for a medical device according to a particular embodiment based on various considerations, include any desired visualization characteristics when the medical device is used with imaging modalities, such as MRI. Examples of suitable configurations include, but are not limited to, a ring, a strip, a plug, a twisted band, a twisted ring, multiple bands attached to each other, multiple rings attached to each other, and other configurations. A circumferential band of material, as best illustrated in FIGS. 4, 5, and 6, is considered particularly advantageous. A wire guide according to an embodiment can include any number of markers, too, and a skilled artisan will be able to select a suitable number of markers for a medical device according to a particular embodiment based on various considerations, including any desired visualization patterns when the wire guide is used with imaging modalities, such as MRI. Examples of suitable numbers include, but are not limited to, one, more than one, two, a plurality, three, more than three, four, five, six, seven, eight, nine, ten, and more than ten.

The marker 150 can be disposed at any suitable axial position relative to the lengthwise axis 102 of the core member 110 and a skilled artisan will be able to select a suitable position for a marker relative to the lengthwise axis of the core member in a wire guide according to a particular embodiment based on various considerations, including any desired visualization patterns when the medical device is used with imaging modalities, such as MRI. As best illustrated in FIGS. 4, 5, and 6, the marker 150 in the example wire guide 100 is positioned proximal to the distal end 114 of the core member 110, but axially within a distal portion 120 of the wire guide 100 that extends from a point beyond the longitudinal midpoint on the lengthwise axis 102 of the core member 110 to the distal end 114 of the core member 110. Other examples of suitable positions include, but are not limited to, within an axial portion of the wire guide 100 that is proximal to the longitudinal midpoint of the core member 110, at the distal end 114 of the core member 110, at the proximal end 112 of the core member 110, at the distal end 134 of the jacket 130, and the proximal end 132 of the jacket 130, and combinations of these positions with multiple markers.

The marker 150 has a susceptibility that is different from the magnetic susceptibility of the core member 110. Accordingly, the marker can be formed of any metal, alloy, or other material that provides the desired relative susceptibility as compared to the susceptibility of the core member 110. A skilled artisan will be able to select a suitable material for the marker in a medical device according to a particular embodiment based on various considerations, including the composition of the reinforcement member in the medical device. Suitable pairings of materials for the core member and the marker in wire guides according to the invention are described in detail below. Examples of suitable materials for the marker include, but are not limited to, metals, such as Titanium, Nickel, and other metals, alloys, such as stainless steel alloys, including 304V stainless steel and 316LVM stainless steel, nickel iron alloys, such as mu-metal, including mu-metal according to ASTM A753 Alloy 4, MUMETAL® magnetic shielding alloy available from Magnetic Shield Corporation of Bensenville, IL, MUMETALL® alloy available from VACUUMSCHMELZE GmbH & Co. KG of Hanau, Germany, and MUSHIELD™ magnetic shielding alloy according to ASTM A753, Alloy 3 available from The MuShield Company of Londonderry, New Hampshire, ferromagnetic materials, paramagnetic materials, alloys containing at least 50% Iron by weight, 316 Stainless Steel, and any other material considered suitable for a particular embodiment. Alternative embodiments include a marker disposed on an external surface of the jacket of the wire guide. For example, a marker can be printed onto or adhered to an external surface of a wire guide. For example, an ink containing a material having a magnetic susceptibility that is greater than the magnetic susceptibility of the core member in a wire guide, such as an ink containing magnetic particles, an ink containing Iron Oxide nanoparticles, or an ink containing Iron Oxide nanoparticles bound to phospholipids, can be printed onto an external surface of the jacket to form a marker in a wire guide according to an embodiment. A marker can be disposed on a surface by other suitable processes, too, such as chemical vapor deposition and plating. Also alternatively, a tape including a material having a magnetic susceptibility that is greater than the magnetic susceptibility of the core member in a wire guide, such as magnetic tape, can be adhered to an external surface of a covering in a wire guide to form a marker in a wire guide according to an embodiment. Selection of a marker, or markers, to include in a wire guide according to a particular embodiment can also be based upon the field strength, or field strengths, within which the wire guide is intended to be used. For example, a wire guide that includes a marker can be utilized to complete one, or more than one, interventional procedure under MRI utilizing one or more field strengths (0.55 T, 1.5 T, or 3.0 T). Material or materials can be selected for a marker or markers in a wire guide according to an embodiment based on these expected field strengths and the expected visual artifacts produced by a marker or markers formed of a particular material and having a particular structural configuration.

The core member in a wire guide according to the invention has a susceptibility that is different from the susceptibility of a marker in the wire guide. Thus, the marker in a wire guide according to the invention has a susceptibility that is different from the susceptibility of the core member in the wire guide. Any pairing of materials for these elements that provides this relative relationship of the susceptibilities for these elements, which is considered critical to the performance of wire guides according to the invention, can be used in a wire guide according to a particular embodiment. Indeed, the core member and the marker can be formed of the same or different materials as long as the relative relationship of the susceptibilities for these elements is provided. In some embodiments, different materials having different magnetic susceptibilities are used for the core member and the marker. In these embodiments, the core member and the marker have different susceptibilities and are formed of materials having different magnetic susceptibilities For these embodiments, a skilled artisan will be able to select a material for one of these elements in a wire guide according to a particular embodiment based on various considerations, including the composition of the other of these elements and any desired performance characteristics or imaging characteristics for the wire guide. Examples of suitable pairings of different materials for the core member and the marker include, but are not limited to, a first material for the core member and a second, different material for the marker, such as a paramagnetic material for the core member and a ferromagnetic material for the marker, an alloy containing less than or equal to 1% Iron by weight for the core member and an alloy containing at least 50% Iron by weight for the marker, a Cobalt Chromium alloy for the core member and a stainless steel for the marker, and a Nickel Cobalt alloy, such as MP35N, for the core member and a stainless steel, such as 304V stainless steel of 316LVM stainless steel, for the marker. In other embodiments, the core member and the marker are formed of the same material. In these embodiments, while the reinforcement member and the marker have different susceptibilities, the core member and the marker have the same magnetic susceptibility. For example, in the illustrated embodiment, the core member 110 and the marker 150 can be formed of the same material, giving the core member 110 and the marker 150 the same magnetic susceptibility. To provide the different susceptibilities for these elements 110, 150, one element, such as the marker 150, can be work-hardened or manipulated in some manner that provides a susceptibility that is different from the susceptibility of the other.

FIG. 6 illustrates another example wire guide 200. Wire guide 200 is similar to wireguide 100 described above and illustrated in FIGS. 1, 2, 3, 4, and 5, except as detailed below. In this embodiment, wire guide 200 includes a core member 210 formed of multiple core segments 210a, 210b, 210c, each of which has an axial length that is different from the axial length of the other core segments 210a, 210b, 210c. A jacket 230 formed of a dielectric material is disposed over all of the core segments 210a, 210b, 210c. Thus, each of the core segments 210a, 210b, 210c is fully encapsulated by the jacket 230.

Core segment 210a has first 260 and second 262 terminal ends. Core segment 210b has first 264 and second 266 terminal ends. Core segment 210c has first 268 and second 270 terminal ends. Thus, in this embodiment, core member 210 is not a continuous core member, but is rather an interrupted core member with internal terminal ends. This structural arrangement may be desirable in wire guides according to particular embodiments, for example. Each of the core segments 210a, 210b, 210c is formed of a first material having a first susceptibility. It is noted, though, that the core segments 210a, 210b, 210c may have different susceptibilities and can be formed of different materials. Also, while wire guide 200 includes multiple core segments 210a, 210b, 210c arranged end-to-end, it is noted that, in other example embodiments, wire guides can include multiple core members that co-extend along a length or portion of a length of the wire guide. For example, a wire guide can include multiple core members arranged side-by-side, wound helically around a central longitudinal axis, or arranged in another suitable structural configuration.

Figure 7:
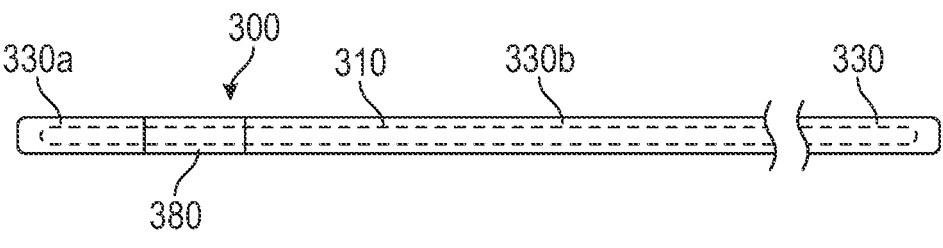
FIG. 7 is a side view, partially broken away, of another example interventional medical device.

FIG. 7 illustrates another example wireguide 300. Wire guide 300 is similar to wireguide 100 described above and illustrated in FIGS. 1, 2, 3, 4, and 5, except as detailed below. Thus, wire guide 300 includes a continuous core member 310 formed of a material having a first susceptibility. A jacket 330 formed of a first dielectric material is disposed over the continuous core member 310 and includes first 330a and second 330b jacket portions. A circumferential band 380 formed of a second dielectric material that is different from the first dielectric material is disposed around the continuous core member 310 and axially between the first 330a and second 330b jacket portions. The circumferential band 380 is attached to the first 330a and second 330 jacket portions, such as with an adhesive or other suitable attachment, and forms a substantially continuous outer surface with the first 330a and second 330b jacket portions. Any suitable dielectric materials can be used for the first and second dielectric materials, as long as they are different materials. For example, the first dielectric material can be a first polymer and the second dielectric material can be a second polymer. Advantageously, the first dielectric material is a polymer and the second dielectric material is a non-polymer. Particularly advantageously, the first dielectric material is a polymer and the second dielectric material is a ceramic.

Figure 8:
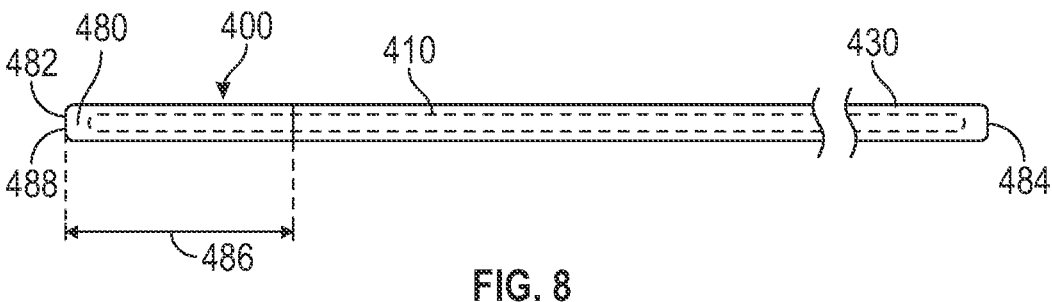
FIG. 8 is a side view, partially broken away, of another example interventional medical device.

FIG. 8 illustrates another example wire guide 400. Wire guide 400 is similar to wireguide 300 described above and illustrated in FIG. 7, except as detailed below. Thus, wire guide 400 includes a continuous core member 410 formed of a material having a first susceptibility. A jacket 430 formed of a first dielectric material is disposed over the continuous core member 410. A circumferential band 480 formed of a second dielectric material that is different from the first dielectric material is disposed around the continuous core member 410. Any suitable dielectric materials can be used for the first and second dielectric materials, as long as they are different materials. For example, the first dielectric material can be a first polymer and the second dielectric material can be a second polymer. Advantageously, the first dielectric material is a polymer and the second dielectric material is a non-polymer. Particularly advantageously, as described below, the first dielectric material is a polymer and the second dielectric material is a ceramic.

In this embodiment, the circumferential band 480 extends from one end 482 of the wire guide 400 toward the other end 484 of the wire guide 400 along an axial length 486 that is less than the full axial length of the wire guide 400. Also in this embodiment, circumferential band 480 is a cap that defines a terminal surface 488 at the end 482 of the wire guide 400. The axial length 486 can be any axial length relative to the full axial length of the wire guide and a skilled artisan will be able to select a suitable axial length for a circumferential band 482 in a wire guide according to a particular embodiment based on various considerations, including the nature of the material from which the circumferential band 482 is formed. Examples of suitable axial lengths relative to the full axial length of the wire guide included, but are not limited to, about 5%, about 10%, about 15%, about 20%, about 25%, about 40%, and about 50%. Advantageously, the axial length of the circumferential band is less than about 20% of the full axial length of the wire guide. Also advantageously, the axial length of the circumferential band is less than about 10% of the full axial length of the wire guide. Inclusion of circumferential band 486, particularly a ceramic circumferential band, in accordance with this embodiment is considered particularly advantageous at least because the ceramic material, positioned on one end of the wire guide, provides the desired dielectric material while also providing a material that is less susceptible to integrity disruptions that a polymer during manual handling of the wire guide at an end during use of the wire guide.

Figure 9:
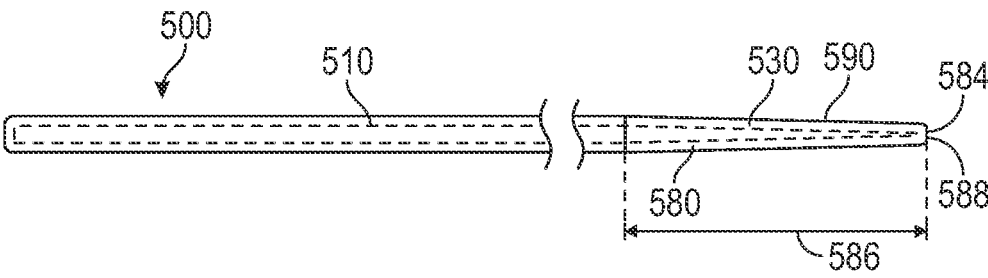
FIG. 9 is a side view, partially broken away, of another example interventional medical device.

FIG. 9 illustrates another example wire guide 500. Wire guide 500 is similar to wireguide 400 described above and illustrated in FIG. 8, except as detailed below. Thus, wire guide 500 includes a continuous core member 510 formed of a material having a first susceptibility. A jacket 530 formed of a first dielectric material is disposed over the continuous core member 510. A circumferential band 580 formed of a second dielectric material that is different from the first dielectric material is disposed around the continuous core member 510. Any suitable dielectric materials can be used for the first and second dielectric materials, as long as they are different materials. For example, the first dielectric material can be a first polymer and the second dielectric material can be a second polymer. Advantageously, the first dielectric material is a polymer and the second dielectric material is a non-polymer. Particularly advantageously, as described below, the first dielectric material is a polymer and the second dielectric material is a ceramic.

In this embodiment, the circumferential band 580 extends from one end 584 of the wire guide 500 toward the other end 582 of the wire guide 500 along an axial length 586 that is less than the full axial length of the wire guide 500. Also in this embodiment, circumferential band 580 is a cap that defines a terminal surface 588 at the end 584 of the wire guide 500. The axial length 586 can be any axial length relative to the full axial length of the wire guide and a skilled artisan will be able to select a suitable axial length for a circumferential band 582 in a wire guide according to a particular embodiment based on various considerations, including the nature of the material from which the circumferential band 582 is formed. Examples of suitable axial lengths relative to the full axial length of the wire guide included, but are not limited to, about 5%, about 10%, about 15%, about 20%, about 25%, about 40%, and about 50%. Advantageously, the axial length of the circumferential band is less than about 20% of the full axial length of the wire guide. Also advantageously, the axial length of the circumferential band is less than about 10% of the full axial length of the wire guide. Inclusion of circumferential band 586, particularly a ceramic circumferential band, in accordance with this embodiment is considered particularly advantageous at least because the ceramic material, positioned on one end of the wire guide, provides the desired dielectric material while also providing a material that is suitable for advancing the end 584 of the wire guide 500 through biological matter, such as blockages within a body vessel, tissue, or other biological matter. Also in this embodiment, circumferential band 580 defines a taper 590, providing a reduced diameter at the end 584 of the wire guide.

Wire guides according to embodiments are useful in performing interventional procedures under MRI.

Figure 10:
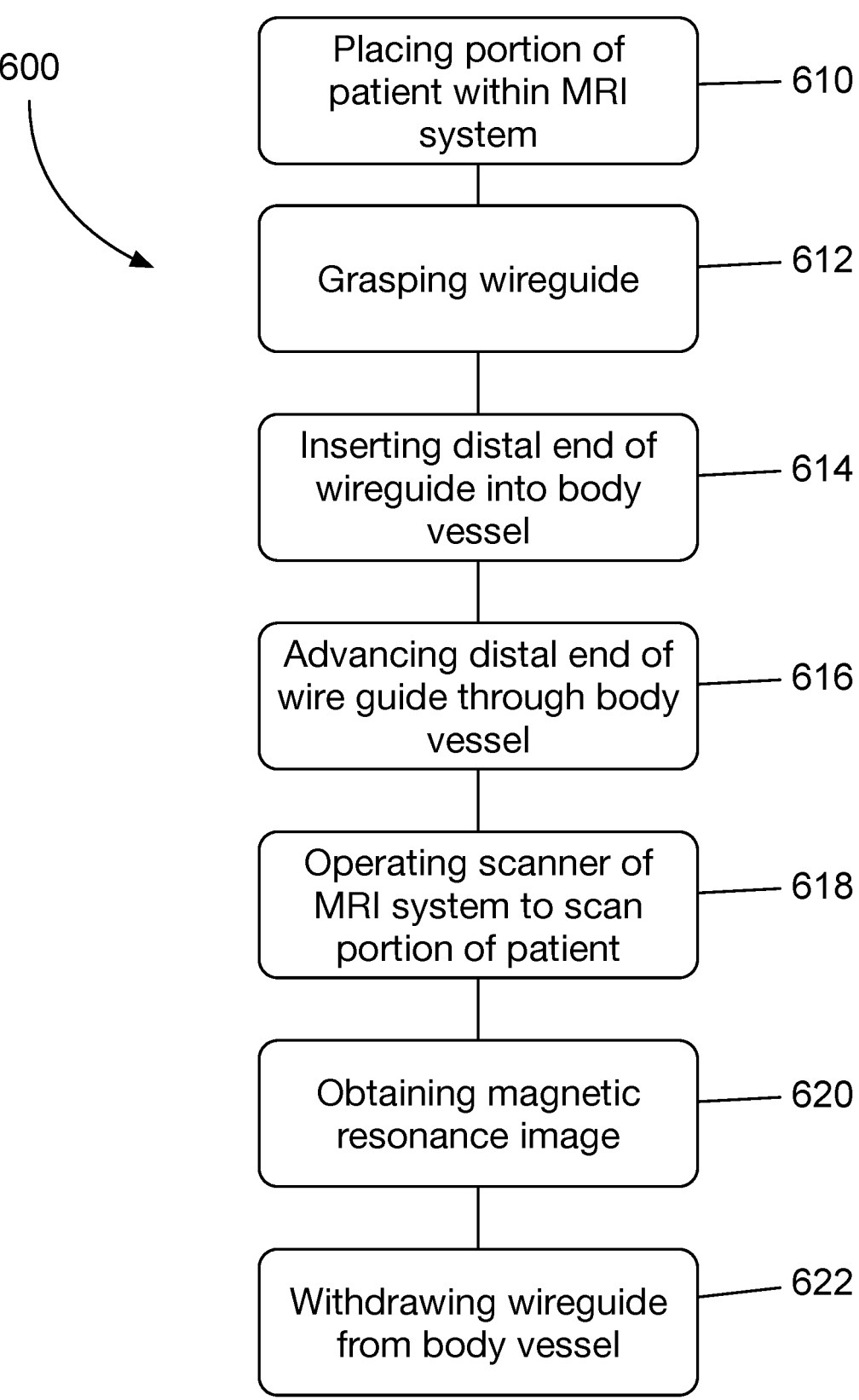
FIG. 10 is a flowchart illustration of an example method of imaging a portion of a body vessel.

FIG. 10 illustrates an example method 600 of imaging a portion of a body vessel.

An initial step 610 comprises placing a portion of a patient within or adjacent an MRI system having a scanner such that a portion of the body vessel is located within the area within which the magnetic field of the scanner of the MRI system will be present once the scanner of the system is activated. Another step 612 comprises grasping a wire guide having a continuous metallic core member and a continuous jacket disposed over the entire core member. Another step 614 comprises inserting the distal end of the wire guide into a body vessel of the patient. Another step 616 comprises advancing the distal end of the wire guide through the body vessel of the patient until the distal end of the wire guide is disposed at a first position within a first portion of the body vessel that is located within the scanner of the MRI system. Another step 618 comprises operating the scanner of the MRI system to scan the portion of the patient that is positioned within the scanner and that includes the first portion of the body vessel. Another step 620 comprises obtaining a magnetic resonance image of the first portion of the body vessel. Another step 622 comprises withdrawing the wire guide from the body vessel.

Step 610 can be performed by any suitable technique and the technique used in a method according to a particular embodiment will depend on various considerations, including the nature and configuration of the MRI system and scanner used and the nature and position of the body vessel to for which imaging is to be performed. Conventional MRI systems typically include a patient support surface, such as a table or bed, that can be moved relative to a bore defined by the MRI system to position a desired portion of the patient within the magnetic field of the scanner. For these MRI systems, step 610 can be performed by moving the patient support system relative to the scanner of the MRI system until the desired portion of the patient is located within the bore of the MRI system. For open, portable, and other MRI systems that do not define a bore within which the patient or portion of the patient can be placed, step 610 can be performed by placing the desired portion of the patient within the area within which the magnetic field of the scanner of the MRI system which will be present once the scanner of the system is activated. For example, for a portable MRI system, the system can be moved to the patient, such as by transporting the portable MRI system to the bedside of a patient, and then moving the portable MRI system relative to a patient support surface on which the patient is positioned, such as a hospital bed, such that the portion of the body vessel is located within the magnetic field of the scanner, or will be located within the area within which the magnetic field of the scanner of the MRI system will be present once the scanner of the MRI system is activated.

For step 610, any suitable portion of a patient can be used, and selection of a suitable portion of a patient during performance of a method according to a particular embodiment can be based on various considerations, including desired images, any treatment intended to be performed, and other considerations. Examples of portions of a patient considered suitable include, but are not limited to, the extremities (e.g., arms, legs), chest, breast, spine, neck, head, abdomen, pelvis, prostate, peri-prostatic structures, tissues surrounding the portions of a patient described herein, and/or any other portion of the patient considered suitable for a method according to a particular embodiment. Also for this step, the patient can be any animal for which imaging is desired, including human beings and other mammals.

Step 612 can be performed by grasping an appropriate wire guide by the hand or using a suitable tool or equipment, such as a robotic arm. Selection of an appropriate wire guide for performance of step 612 is considered important to the performance of the method 600. The wire guide selected should have a continuous metal core member with a jacket that fully encapsulates the core member, such as a jacket that is disposed over the entire length of the core member and that has a length that is greater than the length of the core member. Examples of wire guides suitable for use in performance of step 612 include the example wire guides described in detail below and illustrated in the Figures.

Step 614 can be performed using conventional interventional techniques, such as the Seldinger technique, to introduce the distal end of the wire guide into any suitable body vessel at a point of insertion. For example, a needle can be used to puncture the skin and enter the body vessel. Once access to the body vessel is established in this way, the distal end of the wire guide can be passed through the lumen of the needle and into the body vessel. The needle can then be withdrawn over the proximal end of the wire guide, leaving the distal end of the wire guide extending into the body vessel. Also, the distal end of the wire guide can be inserted into any suitable body vessel. The body vessel into which the distal end of the wire guide is inserted during performance of a method according to a particular embodiment can be selected based on a desired location for scanning, imaging, treatment, or other considerations. Examples of suitable body vessels include, but are not limited to vessels of the peripheral vasculature. Step 614 can be performed before or after step 610 is performed, or while step 610 is being performed. A skilled artisan will be able to select an appropriate relative ordering of steps 610 and 614 based on a variety of considerations, including the nature of the MRI system and scanner and other considerations.

Step 616 can be performed by applying a distally directed force on a portion of the wire guide that remains external to the body of the patient, such as the proximal end of the wire guide or an intermediate portion of the wire guide, such that the distal end of the wire guide moves axially within the lumen of the body vessel, away from the point of insertion into the body vessel. Step 616 is performed until the distal end of the wire guide is disposed at a first position within a first portion of the body vessel, the first portion being a portion of interest for subsequent step 618 of operating the scanner of the MRI system and step 620 of obtaining an image.

Step 618 can be performed by operating the MRI system to scan the portion of the patient located within the scanner of the MRI system by performance of step 610. Step 618 can be performed using any suitable MRI parameters applicable for the scanner of the MRI system, such as gradient refocusing echo imaging, spin echo imaging, true fast imaging with steady-state precession, fast low flip angle shot spoiled gradient-echo imaging, field strength, such as 0.55 T, 1.5 T, 3 T, between about 0.055 T and 1.5 T, and a field strength less than 1 T, slice thickness, flip angle, field-of-view, resolution, gradient fields, and any other MRI parameter or parameters considered suitable for a method according to a particular embodiment.

Step 620 can be performed by obtaining the image from the scanner of the MRI system used in step 618. For the step 620 of obtaining a magnetic resonance image of the first portion of the body vessel, a single still image can be obtained. Also, and optionally, this step 620 can be repeated any desired number of times to obtain multiple magnetic resonance images that can be grouped as a cine to show motion. Furthermore, as an alternative to, or in addition to, obtaining an image, a step of visualizing the wire guide, a step of visualizing a marker or markers associated with the wire guide, or both, can be included in the method 600.

Step 622 can be performed by applying a proximally directed force on a portion of the wire guide that remains external to the body of the patient, such as the proximal end of the wire guide or an intermediate portion of the wire guide, such that the distal end of the wire guide moves axially within the lumen of the body vessel, toward the point of insertion into the body vessel. This step 622 is performed until the distal end of the wire guide passes through the point of insertion and the wire guide completely exits the body lumen. Ultimately, this step 622 results in the wire guide exiting the body of the patient. At this point, performance of the method 600 is complete.

Step 616, 618, and 620 can be performed discretely and sequentially. For example, performance of step 618 can be initiated after step 616 is completed. Also, performance of step 620 can be initiated after step 618 is completed. Other sequencing of these steps is possible, though, and are considered advantageous for methods according to particular embodiments. For example, if multiple images are desired to aid in navigation of a wire guide through a body vessel, each of steps 618 and 620 can be performed multiple times while step 616 is being performed. That is, the step 618 of operating the scanner of the MRI system to scan the portion of the patient that is positioned within the scanner and that includes the first portion of the body vessel and the step 620 of obtaining a magnetic resonance image of the first portion of the body vessel can be performed multiple times while the step 616 of advancing the distal end of the wire guide through the body vessel of the patient is being performed. In these examples, steps 618 and 620 can be performed any suitable number of times during the performance of step 616, and a skilled artisan will be able to select an appropriate number of times for each step for inclusion in a method according to a particular embodiment based on various considerations, including the capabilities of the MRI system, the nature of the body vessel and any navigation challenges it presents, and other considerations. Examples of suitable numbers of times for the performance of step 618 and 620 while step 616 is being performed include, but are not limited to, one, two, more than two, three, a plurality, four, five, six, seven, eight, nine, ten, more than ten, eleven, twelve, more than twelve, twenty, fifty, one hundred, and one thousand.

Performance of the method provides one or more images of the portion of the body vessel that can be used for various purposes, including educational purposes, research purposes, diagnostic purposes, treatment purposes, and informational purposes.

FIG. 11 illustrates an example method 700 of performing interventional medical treatment under MRI.

An initial step 710 comprises placing a portion of a patient within or adjacent an MRI system having a scanner such that a portion of the body vessel is located within the area within which the magnetic field of the scanner of the MRI system will be present once the scanner of the system is activated. Another step 712 comprises grasping a wire guide having a continuous metallic core member and a continuous jacket disposed over the entire core member. Another step 714 comprises inserting the distal end of the wire guide into a body vessel of the patient. Another step 716 comprises advancing the distal end of the wire guide through the body vessel of the patient until the distal end of the wire guide is disposed within a first portion of the body vessel having a first position. Another step 718 comprises operating the scanner of the MRI system to scan the portion of the patient that is positioned within the scanner and that includes the first portion of the body vessel. Another step 720 comprises obtaining a magnetic resonance image of the first portion of the body vessel. Another step 722 comprises grasping a medical device having a medical device proximal end and a medical device distal end and includes an elongate member defining a lumen. Another step 724 comprises advancing the distal end of the medical device over the wire guide into the body vessel of the patient until the distal end of the medical device reaches the point of treatment within the body vessel. Another step 726 comprises manipulating a proximal end of the medical device to produce a manipulation of the distal end of the medical device at the point of treatment. Another step 728 comprises withdrawing the medical device from the body vessel. Another step 730 comprises withdrawing the wire guide from the body vessel.

Step 710 can be performed by any suitable technique and the technique used in a method according to a particular embodiment will depend on various considerations, including the nature and configuration of the MRI system used and the nature and position of the body vessel for which imaging is to be performed. Conventional MRI systems typically include a patient support surface, such as a table or bed, that can be moved relative to the scanner of the MRI system to position a desired portion of the patient within the scanner. For these MRI systems, step 710 can be performed by moving the patient support system relative to the scanner of the MRI system until the desired portion of the patient is located within the scanner of the MRI system. As described above with method 700, this step 710 can be performed with other, non-bore defining MRI systems, such as open MRI systems and portable MRI systems, too. For example, for portable MRI systems, step 710 can be performed by moving the portable MRI system relative to the patient to place the desired portion of the patient within the area within which the magnetic field of the scanner of the MRI system will be present once the scanner of the system is activated.

For step 710, any suitable portion of a patient can be used, and selection of a suitable portion of a patient during performance of a method according to a particular embodiment can be based on various considerations, including the location of the desired point of treatment, the nature of the treatment intended to be performed, and other considerations. Examples of portions of a patient considered suitable include, but are not limited to, the extremities (e.g., arms, legs), chest, breast, spine, neck, head, abdomen, pelvis, prostate, peri-prostatic structures, tissues surrounding the portions of a patient described herein, and/or any other portion of the patient considered suitable for a method according to a particular embodiment. Also for this step, the patient can be any animal for which imaging is desired, including human beings and other mammals.

Step 712 can be performed by grasping an appropriate wire guide by the hand or using a suitable tool or equipment, such as a robotic arm. Selection of an appropriate wire guide for performance of step 712 is considered important to the performance of the method 700. The wire guide selected should have a continuous metal core member with a jacket that fully encapsulates the core member, such as a jacket that is disposed over the entire length of the core member and that has a length that is greater than the length of the core member. Examples of wire guides suitable for use in performance of step 712 include the example wire guides described in detail below and illustrated in the Figures.

Step 714 can be performed using conventional interventional techniques, such as the Seldinger technique, to introduce the distal end of the wire guide into any suitable body vessel at a point of insertion. For example, a needle can be used to puncture the skin and enter the body vessel. Once access to the body vessel is established in this way, the distal end of the wire guide can be passed through the lumen of the needle and into the body vessel. The needle can then be withdrawn over the proximal end of the wire guide, leaving the distal end of the wire guide extending into the body vessel. Also, the distal end of the wire guide can be inserted into any suitable body vessel. The body vessel into which the distal end of the wire guide is inserted during performance of a method according to a particular embodiment can be selected based on a desired location for scanning, imaging, treatment, or other considerations. Examples of suitable body vessels include, but are not limited to vessels of the peripheral vasculature. Step 714 can be performed before or after step 710 is performed, or while step 710 is being performed. A skilled artisan will be able to select an appropriate relative ordering of steps 710 and 714 based on a variety of considerations, including the nature of the MRI system and scanner and other considerations.

Step 716 can be performed by applying a distally directed force on a portion of the wire guide that remains external to the body of the patient, such as the proximal end of the wire guide or an intermediate portion of the wire guide, such that the distal end of the wire guide moves axially within the lumen of the body vessel, away from the point of insertion into the body vessel. Step 716 is performed until the distal end of the wire guide is disposed at the a first position within a first portion of the body vessel, the first portion being a portion of interest for subsequent step 718 of operating the scanner of the MRI system and step 720 of obtaining an image.

Step 718 can be performed by operating the MRI system to scan the portion of the patient located within the scanner of the MRI system by performance of step 710. Step 718 can be performed using any suitable MRI parameters applicable for the scanner of the MRI system, such as gradient refocusing echo imaging, spin echo imaging, true fast imaging with steady-state precession, fast low flip angle shot spoiled gradient-echo imaging, field strength, such as 0.55 T, 1.5 T, 3 T, between about 0.055 T and 1.5 T, and a field strength less than 1 T, slice thickness, flip angle, field-of-view, resolution, gradient fields, and any other MRI parameter or parameters considered suitable for a method according to a particular embodiment.

Step 720 can be performed by obtaining the image from the scanner of the MRI system used in step 718. For the step 720 of obtaining a magnetic resonance image of the first portion of the body vessel, a single still image can be obtained. Also, and optionally, this step 720 can be repeated any desired number of times to obtain multiple magnetic resonance images that can be grouped as a cine to show motion. Furthermore, as an alternative to, or in addition to, obtaining an image, a step of visualizing the wire guide, a step of visualizing a marker or markers associated with the wire guide, or both, can be included in the method 700.

Step 722 can be performed by grasping an appropriate medical device by the hand or using a suitable tool. Any suitable medical device can be used in step 722 as long as the medical device includes an elongate member that defines a lumen configured to receive the wire guide. The medical device selected for use in a method according to a particular embodiment will depend on various considerations, including the nature of the body vessel, the point of treatment, and the effect desired by performance of the method. Examples of suitable medical device include, but are not limited to, catheters, balloon catheters, cannula, biopsy device, retrieval devices, and other medical devices. Furthermore, the medical device can include a deployable medical device that can be deployed from the medical device in step 726, described below, and left within the body vessel after performance of the method 700. For example, a medical device used in this step 722 can include a stent, such as a self-expandable stent, a balloon expandable stent, or other stent, a graft device, such as a stent graft, a valve, such as a prosthetic heart valve or other valve device, a filter, or any other type of deployable medical device.

Step 724 can be performed by applying a distally directed force on a portion of the medical device that remains external to the body of the patient, such as the proximal end of the medical device or an intermediate portion of the medical device, such that the distal end of the medical device moves axially within the lumen of the body vessel, away from the point of insertion into the body vessel. Step 724 is performed until the distal end of the medical device reaches the desired point of treatment within the body vessel.

Step 726 can be performed in any suitable manner that is appropriate for the medical device advanced through the body vessel in step 724. For example, if the medical device is a balloon catheter, step 726 can be performed by passing an inflation fluid into a connector on the proximal end of the device and through an inflation lumen of the medical device such that the balloon on the distal end inflates at the point of treatment. Additional manipulations can be included in the performance of step 726 as appropriate for the medical device, too.

Step 728 can be performed by applying a proximally directed force on a portion of the medical device that remains external to the body of the patient, such as the proximal end of the medical device or an intermediate portion of the medical device such that the distal end of the medical device moves axially within the lumen of the body vessel and along the wire guide, toward the point of insertion into the body vessel. This step 728 is performed until the distal end of the medical device passes through the point of insertion and the medical device completely exits the body vessel. Ultimately, this step 728 results in the medical device exiting the body of the patient.

Step 730 can be performed by applying a proximally directed force on a portion of the wire guide that remains external to the body of the patient, such as the proximal end of the wire guide or an intermediate portion of the wire guide, such that the distal end of the wire guide moves axially within the lumen of the body vessel, toward the point of insertion into the body vessel. This step 730 is performed until the distal end of the wire guide passes through the point of insertion and the wire guide completely exits the body lumen. Ultimately, this step 730 results in the wire guide exiting the body of the patient. At this point, performance of the method 700 is complete.

Various steps of method 700 can be performed discretely and sequentially. For example, performance of step 718 can be initiated after step 716 is completed. Also, performance of step 720 can be initiated after step 718 is completed. Also, performance of step 724 can be initiated after step 720 is completed. Other sequencing of these steps is possible, though, and are considered advantageous for methods according to particular embodiments. For example, if multiple images are desired to aid in navigation of a wire guide through a body vessel, each of steps 718 and 720 can be performed multiple times while step 716 is being performed. That is, the step 718 of operating the scanner of the MRI system to scan the portion of the patient that is positioned within the scanner and that includes the first portion of the body vessel and the step 720 of obtaining a magnetic resonance image of the first portion of the body vessel can be performed multiple times while the step 716 of advancing the distal end of the wire guide through the body vessel of the patient is being performed. In these examples, steps 718 and 720 can be performed any suitable number of times during the performance of step 716, and a skilled artisan will be able to select an appropriate number of times for each step for inclusion in a method according to a particular embodiment based on various considerations, including the capabilities of the MRI system, the nature of the body vessel and any navigation challenges it presents, and other considerations.

Also, if multiple images are desired to aid in navigation of the medical device over the wire guide and through the body vessel, each of steps 718 and 720 can be performed multiple times while step 724 is being performed. That is, the step 718 of operating the scanner of the MRI system to scan the portion of the patient that is positioned within the scanner and that includes the first portion of the body vessel and the step 720 of obtaining a magnetic resonance image of the first portion of the body vessel can be performed multiple times while the step 724 of advancing the distal end of a medical device over the wire guide into the body vessel of the patient is being performed. In these examples, steps 718 and 720 can be performed any suitable number of times during the performance of step 724, and a skilled artisan will be able to select an appropriate number of times for each step for inclusion in a method according to a particular embodiment based on various considerations, including the capabilities of the MRI system, the nature of the body vessel and any navigation challenges it presents, and other considerations. Examples of suitable numbers of times for the performance of step 718 and 720 while step 724 is being performed include, but are not limited to, one, two, more than two, three, a plurality, four, five, six, seven, eight, nine, ten, more than ten, eleven, twelve, more than twelve, twenty, fifty, one hundred, and one thousand.

Also, if multiple images are desired to monitor manipulation of the distal end of the medical device at the point of treatment, each of steps 718 and 720 can be performed multiple times while step 726 is being performed. That is, the step 718 of operating the scanner of the MRI system to scan the portion of the patient that is positioned within the scanner and that includes the first portion of the body vessel and the step 720 of obtaining a magnetic resonance image of the first portion of the body vessel can be performed multiple times while the step 726 of manipulating a proximal end of the medical device to produce a manipulation of the distal end of the medical device at the point of treatment is being performed. In these examples, steps 718 and 720 can be performed any suitable number of times during the performance of step 726, and a skilled artisan will be able to select an appropriate number of times for each step for inclusion in a method according to a particular embodiment based on various considerations, including the capabilities of the MRI system, the nature of the body vessel and any navigation challenges it presents, and other considerations. Examples of suitable numbers of times for the performance of step 718 and 720 while step 726 is being performed include, but are not limited to, one, two, more than two, three, a plurality, four, five, six, seven, eight, nine, ten, more than ten, eleven, twelve, more than twelve, twenty, fifty, one hundred, and one thousand.

Performance of the method provides one or more images of the portion of the body vessel that can be used for various purposes, including educational purposes, research purposes, diagnostic purposes, treatment purposes, and informational purposes.

FIG. 12 illustrates an example method 800 of performing interventional medical treatment under MRI. The method 800 is similar to the method 700 described above, except as detailed below.

An initial step 810 comprises placing a portion of a patient within or adjacent an MRI system having a scanner such that a portion of the body vessel is located within the area within which the magnetic field of the scanner of the MRI system will be present once the scanner of the system is activated. Another step 812 comprises grasping a wire guide having a continuous metallic core member and a continuous jacket disposed over the entire core member. Another step 814 comprises inserting the distal end of a wire guide into a body vessel of the patient. Another step 816 comprises advancing the distal end of the wire guide through the body vessel of the patient until the distal end of the wire guide is disposed within a first portion of the body vessel having a first position. Another step 818 comprises operating the scanner of the MRI system to scan the portion of the patient that is positioned within the scanner and that includes the first portion of the body vessel. Another step 820 comprises obtaining a magnetic resonance image of the first portion of the body vessel. Another step 822 comprises grasping a medical device having a medical device proximal end and a medical device distal end and includes an elongate member defining a lumen. Another step 824 comprises advancing the distal end of the medical device over the wire guide into the body vessel of the patient until the distal end of the wire guide reaches the point of treatment within the body vessel. Another step 826 comprises manipulating a proximal end of the medical device to produce a manipulation of the distal end of the medical device at the point of treatment. Another step 828 comprises withdrawing the medical device from the body vessel. Another step 830 comprises grasping a second medical device having a second medical device proximal end and a second medical device distal end and includes an elongate member defining a lumen. Another step 832 comprises advancing the distal end of a second medical device over the wire guide into the body vessel of the patient until the distal end of the second medical device reaches the point of treatment within the body vessel. Another step 834 comprises manipulating the proximal end of the second medical device to produce a manipulation of the distal end of the second medical device at the point of treatment. Another step 836 comprises withdrawing the second medical device from the body vessel. Another step 838 comprises withdrawing the wire guide from the body vessel.

As described above with method 600 and method 700, step 810 can be performed by moving the patient relative to the MRI system, such as with MRI systems that define a bore into which the patient is positioned for an imaging procedure. Also, step 810 can be performed by moving a portable MRI system relative to the patient to position the patient, or a portion of the patient, within the area within which the magnetic field of the scanner of the MRI system will be present once the scanner of the system is activated.

Step 814 can be performed before or after step 810 is performed, or while step 814 is being performed. A skilled artisan will be able to select an appropriate relative ordering of steps 810 and 814 based on a variety of considerations, including the nature of the MRI system and scanner and other considerations.

In some methods, it may be desirable to pre-load a wire guide into a medical device having an elongate member defining a lumen. In these methods, the distal end of the medical device can be advanced substantially over the wire guide prior to inserting the distal end of the wire guide into the body vessel. In these methods, the distal end of the medical device is advanced over the wire guide until only a relatively small portion of the wire guide extends beyond the distal end of the medical device. The wire guide and medical device are then inserted into the body vessel and navigated through the body vessel together.

Methods of making a wire guide and methods of making a plurality of wire guides are also provided.

Figure 13:
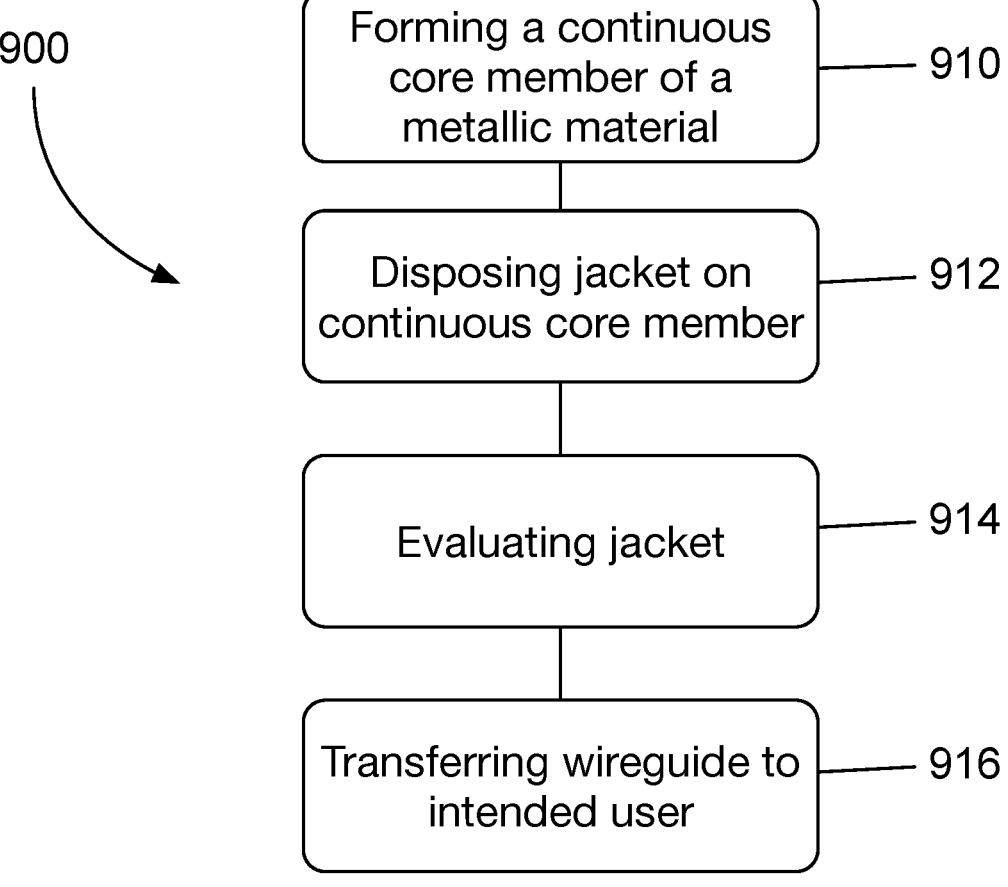
FIG. 13 is a flowchart representation of an example method of making a wire guide.

FIG. 13 illustrates an example method of making a wire guide 900. An initial step 910 comprises forming a continuous core member of a metallic material, the continuous core member having an outer surface. Another step 912 comprises disposing a jacket on the continuous core member such that the outer surface of the core member is in continuous contact with the jacket and such that no portion of the outer surface of the core member is exposed to the external environment surrounding the wire guide. An optional step 914 comprises evaluating the jacket to determine if the outer surface of the core member is fully encapsulated by the jacket, in continuous contact with the jacket, or both. Another optional step 916 comprises transferring the wire guide to an intended user of the wireguide only if the evaluating step 916 results in a determination that the outer surface of the core member is in continuous contact with the jacket.

Step 910 can be performed using any suitable process or technique, including cutting a length of a core member from a stock supply of core member material. Furthermore, any suitable material can be used in the performance of step 910, as described above in relation to the core member of the example wire guides described herein. To form a wire guide according to an embodiment, the material should be a metallic material. Examples of metallic materials considered suitable for forming the core member during the performance of step 910 include, but are not limited to, shape memory alloys, including nickel-titanium alloys such as Nitinol, Superelastic Nitinol SE508 straight with black oxide, matte finished Nitinol, polished Nitinol, combinations of those described herein, and any other metallic materials considered suitable. Step 910 can include various processes and techniques commonly used in the formation of metallic wire guides, including grinding an end to form a desirable tip shape.

Step 912 can be performed using any suitable process or technique, including extruding a polymeric material over the continuous core member to form the jacket, reflowing a polymeric material over the continuous core member to form the jacket, and other suitable processes and techniques.

If included, step 914 can be performed by performing a visual inspection of the jacket to identify any disruptions in the continuous nature of the jacket, performing a visual inspection of the jacket to determine if any portion of the continuous core member is visible; hydrating the continuous core member and determining if any fluid leaks through the jacket, evaluating conduction, induction, or both properties of the core member, and other suitable visual inspection, leak testing, or other suitable quality control techniques. Multiple steps can be included for evaluating the jacket, if desired, such as the leakage testing steps described in detail below.

If included, step 916 can be performed by shipping a wire guide to a purchased, an end user, or an agent of an end user, after determining that the outer surface of the core member is in continuous contact with the jacket.

In alternative methods of making a wire guide, two or more segments that each include a continuous core member and a jacket surrounding the continuous core member can be joined by placing the segments end to end relative to each other, as in a series, and reflowing the jackets by heat treatment to for a continuous wire guide having a continuous jacket that fully encapsulates the series of continuous core members from the previously individual segments. The positioning of the segments and the reflowing of the jackets can be performed in a manner such that the individual continuous core members are abutting each other in the final wire guide, with no insulating material between them, or such that a portion of the jacket is disposed between the individual continuous core members following the reflowing of the jacket. This alternative method can be advantageous for inclusion of distal ends having a jacket comprising a different dielectric material than a jacket of another segment used for the main body of a wire guide, for example.

Figure 14:
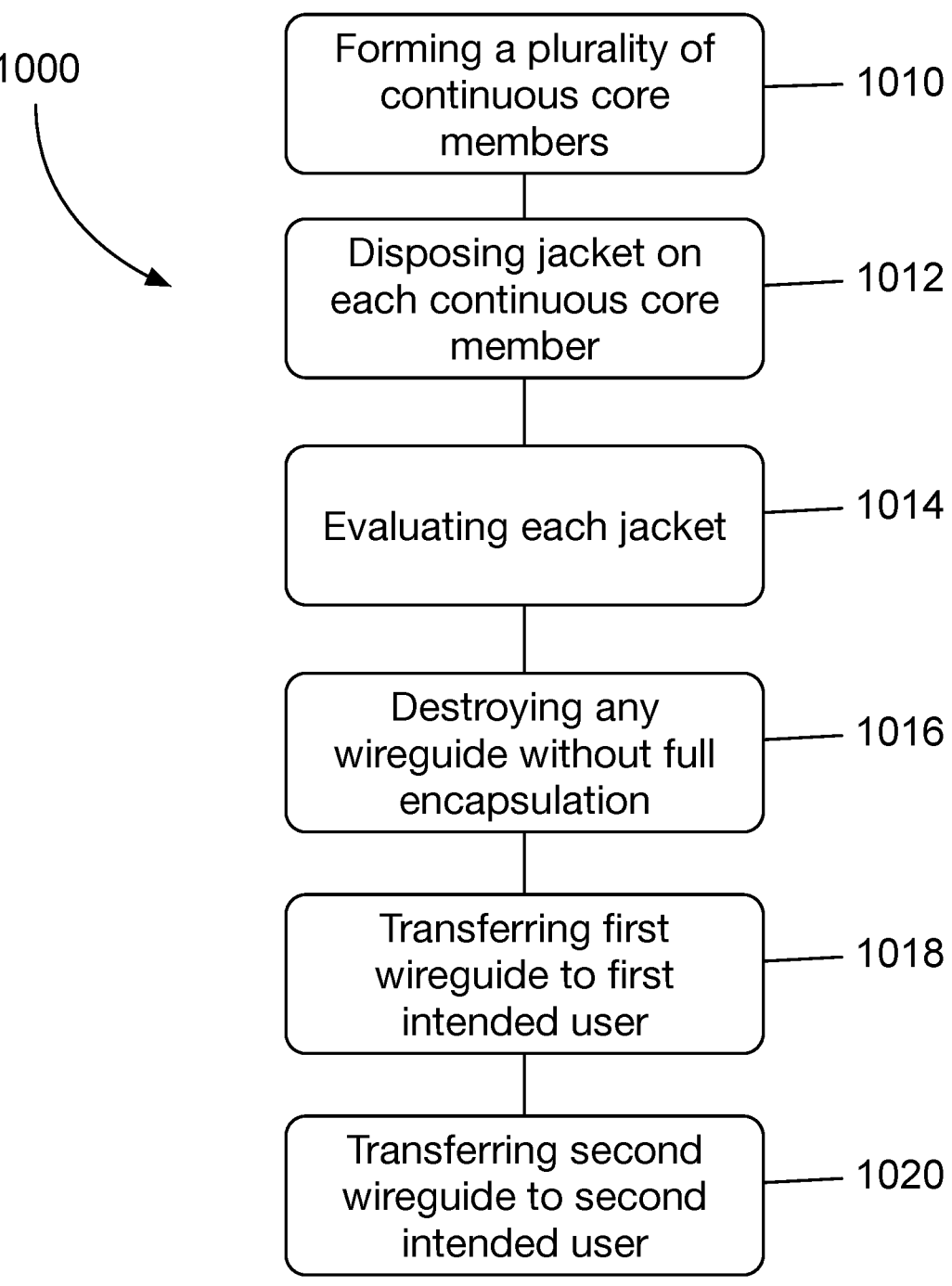
FIG. 14 is a flowchart representation of an example method of making a plurality of wire guides.

FIG. 14 illustrates an example method of making a plurality of wire guides 1000. An initial step 1010 comprises forming a plurality of continuous core members, each continuous core member of the plurality of continuous core members formed of a metallic material and having an outer surface. Another step 1012 comprises disposing a jacket comprising one or more dielectric materials on the outer surface of a continuous core member such that the continuous core member is fully encapsulated by the jacket. This step 1012 can be performed such that the outer surface of the core member is in continuous contact with the jacket. This step 1012 is repeated for each continuous core member formed in step 1010. Another step 1014 comprises evaluating each jacket to determine if the continuous core member associated with the jacket in step 1012 is fully encapsulated by the jacket. An optional step 1016 comprises destroying any wire guides from the plurality of wire guides for which the evaluating step results in a determination that the continuous core member is not fully encapsulated by a jacket. Another optional step 1018 comprises transferring a first wire guide to a first intended user only if the evaluating step 1014 results in a determination that the continuous core member is fully encapsulated by a jacket. Another optional step 1020 comprises transferring a second wire guide to a second intended user only if the evaluating step 1014 results in a determination that the continuous core member is fully encapsulated by a jacket.

Methods of making a wire guide and methods of making a plurality of wire guides can leverage the metal of the continuous core member and the dielectric nature of the jacket in a step or steps for evaluating the encapsulation of the continuous core member by the jacket in each wire guide made by the relevant method. For example, a method can include steps applying an electric current to one end of the continuous core member and measuring the current at the opposite end of the continuous core member to determine if leakage of the applied current is occurring. If leakage is detected, the wire guide can be rejected as likely having a jacket that does not fully encapsulate the continuous core member. One particular method includes the steps of submerging a wire guide in a conductive fluid, such as physiological saline, electrically coupling the continuous core member of the wire guide to a source of electric current to induce current flow in the continuous core member, and measuring current in the conductive fluid to determine if leakage of the applied current into the conductive fluid is occurring. A step of rejecting the wire guide if leakage of current is detected can be included. Detecting leakage of current is considered particularly advantageous as a quality control measure in methods of making a wire guide and methods of making a plurality of wire guides at least because it is believed that leakage of current will correlate with temperature rise of the wire guide under MRI. Identification of a wire guide that demonstrates leakage of electrical current is believed to be a reliable indicator of a wire guide that will demonstrate elevated heating under MRI due to less than full encapsulation of the continuous core member by the jacket.

Specific Examples

Figure 15:
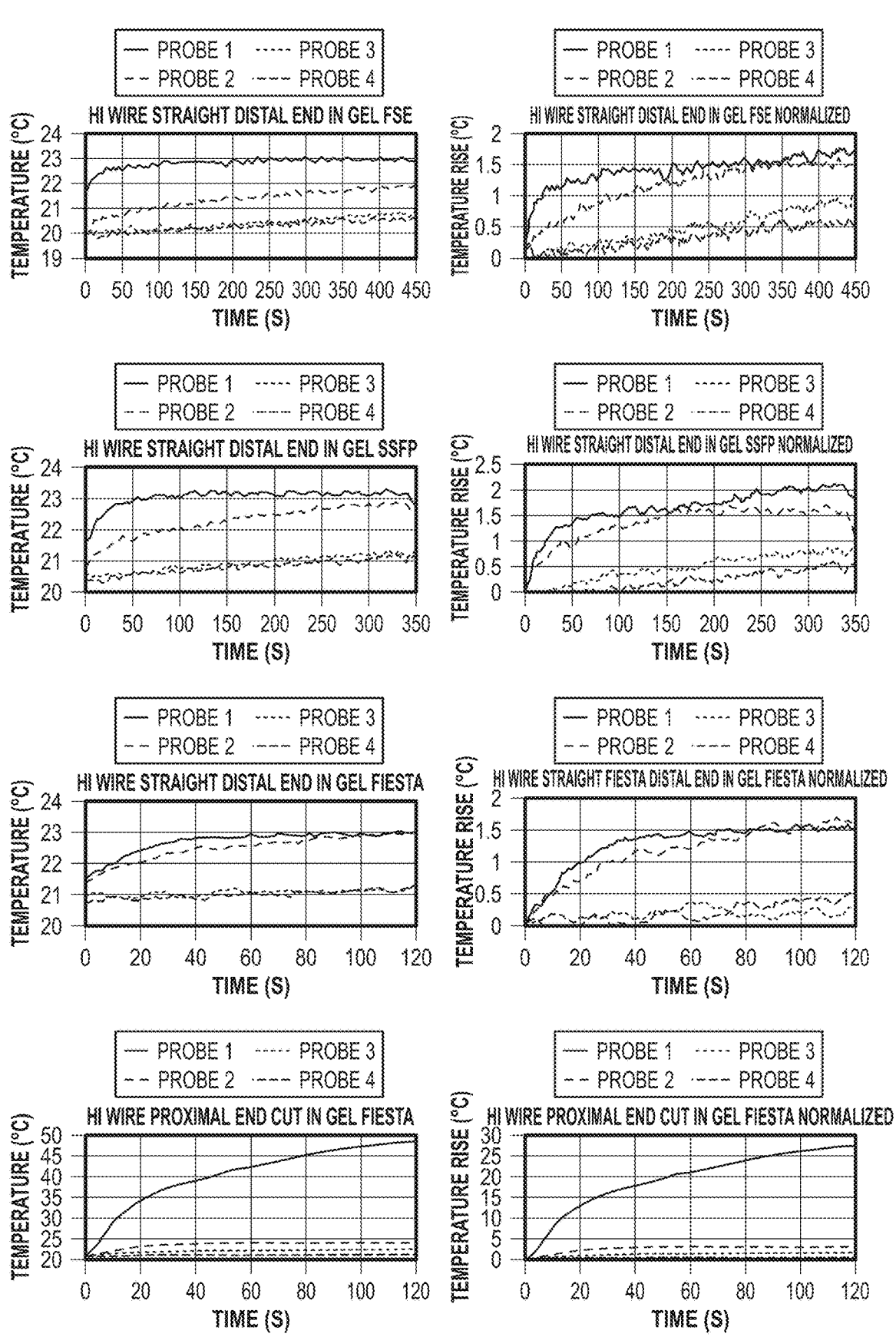
FIG. 15 illustrates graphical representations of raw RF-induced heating for various test wire guide constructions over 2-7 minutes of scanning in a 1.5 T MRI system. Panels on the left represent measured temperature for scans of a wire guide having a continuous nitinol core; panels on the right represent temperature rise normalized to the initial temperature for the corresponding panel on the left.

FIG. 15 includes graphical representation of raw RF-induced heating for various test wire guide constructions over 2-7 minutes of scanning in a 1.5 T MRI system. Measured temperature for the four scans of a wire guide having a continuous Nitinol core covered entirely by a jacket (HiWire® Nitinol core wire guide available from Cook Medical of Bloomington, IN) is shown in the panels on the left and temperature rise normalized to the initial temperature is shown on the panels on the right. The top three sets of panels reflect data for wire guides having fully intact jackets; the bottom two panels reflect data for wire guides in which the proximal end was cut to expose the proximal terminal surface of the wire guide prior to scanning in the MRI system. Data from four separate temperature probes are included.

FIG. 16 presents a table of experimental data showing maximum temperature rise for a) a wire guide having a continuous Nitinol core covered entirely by a jacket (Hi-Wire® Nitinol core wire guide available from Cook Medical of Bloomington, IN), and b) a wire guide having a segmented construction. Considering the teaching of the art, which suggests that a segmented construction is necessary to avoid undesirable RF heating under MRI, this data surprisingly reveals that a wire guide having a fully intact jacket on a continuous nitinol core did not show the expected significant RF heating in an MRI scanner. Data from four separate temperature probes are included.

Also surprisingly, the data reflected in the bottom two panels of FIG. 15 demonstrate that partial insulation in a wire guide by a jacket (i.e., the test wire guides in which the proximal end was cut to expose the proximal terminal surface of the wire guide prior to scanning in the MRI system) results in increased heating, which is believed to be due to a concentration of all electromagnetic propagating waves on the small area of the exposed terminal surfaces of the core member, and the inability of these waves to escape the insulation provided by the jacket along the length of the continuous core member. Based on this, the inventors believe that a wire guide having a continuous core that is fully covered by a jacket will exhibit less heating than that exhibited by a bare continuous core in the same environment, and that a continuous core that is covered by a jacket but that has a bare end of the core member exposed will exhibit even greater temperature rise in the same environment. For at least this reason, inspection of the jacket in wire guides according to the invention, and for potential exposure of the core member to the external environment surrounding the wire guide, is considered important.

Computational modeling and simulation (CM&S) was used to evaluate normalized heating of biological tissue due to radiofrequency (RF) heating. MRI scanners create images using a large static magnetic field (typically 1.5 T but also include 3 T, 1.2 T and low field scanners 0.7 T and 0.55 T), three gradient magnetic fields, and a set of coils that transmit and receive radiofrequency (RF) waves. Clinical MRI systems typically use an RF body coil to transmit RF energy which in turn heats the surrounding tissues. Finite Element Analysis (FEA) of a typical covered wire guide in an ASTM F2182 gel phantom was conducted using COMSOL Multiphysics® v6.0 to quantify the normalized heating of tissue as a function of insulated covering thickness and electrical conductivity as presented in the tables illustrated in FIGS. 17 and 18. The table illustrated in FIG. 19 presents electrical conductivity for some typical wire guide insulating materials.

COMSOL's RF module solves Maxwell's equations subject to initial and boundary conditions and constitutive material properties. A frequency-domain wave equation is solved for the electric field (E) shown in Equation 1 presented in FIG. 20. The eigenvalue problem is solved at frequency ($\omega$), given the magnetic permeability of a vacuum ($\mu_0$), the relative magnetic permeability ($\mu_r = \mu/\mu_0$), the electrical permittivity of a vacuum ($\varepsilon_0$), the relative electrical permittivity ($\varepsilon_r = \varepsilon/\varepsilon_0$), and the electrical conductivity ($\sigma$) of the material.

COMSOL's heat transfer module solves the heat equation for heat conduction in a solid (Equation 2, presented in FIG. 21) subject to initial and boundary conditions. The transient heat equation is solved for temperature (T), given time (t), a heat source (q) solved for in the electromagnetic simulation, the density ($\rho$), the specific heat ($c_p$), and the thermal conductivity (k) of the material. Only in-vivo simulations included the perfusion term in the bioheat equation.

Maxwell's equations and the heat equation are coupled in COMSOL using Joule heating, also known as resistive heating, as the heat source in the heat equation. Joule heating is the process by which the passage of electric current (J) through a conductor releases heat (q) as shown in Equation 3, presented in FIG. 22, given the electric field (E) from Equation 1.

Those with ordinary skill in the art will appreciate that various modifications and alternatives for the described and illustrated examples can be developed in light of the overall teachings of the disclosure, and that the various elements and features of one example described and illustrated herein can be combined with various elements and features of another example without departing from the scope of the invention. Accordingly, the particular arrangement of elements and steps disclosed herein have been selected by the inventor(s) simply to describe and illustrate examples of the invention and are not intended to limit the scope of the invention or its protection, which is to be given the full breadth of the appended claims and any and all equivalents thereof.

What is claimed is:

1. A method of imaging a portion of a body vessel of a patient using MRI, said method comprising:

placing a portion of said patient within an MRI system having a scanner such that a portion of said body vessel is located within the scanner;

grasping a wire guide having a wire guide proximal end and a wire guide distal end and comprising a continuous core member, a continuous jacket disposed over and fully encapsulating the entire core member, and a marker disposed on the core member, the core member formed of a first metallic material and having a first length and an outer surface in contact with the jacket, the first length being between 50 centimeters and 350 centimeters, the jacket disposed over the marker and having a second length that is greater than the first length, and the marker formed of a second metallic material;

inserting the wire guide distal end into said body vessel;

advancing the wire guide distal end through said body vessel until the wire guide distal end is disposed at a first position within a first portion of said body vessel that is located within the scanner of the MRI system;

operating the scanner of the MRI system to scan the portion of the patient that is positioned within the scanner and that includes the first portion of the body vessel;

obtaining a magnetic resonance image of the first portion of the body vessel; and withdrawing the wire guide from the body vessel.

2. The method of claim 1, wherein the jacket is formed of a dielectric material.

3. The method of claim 1, wherein the jacket is formed of a polymeric material.

4. The method of claim 1, wherein the outer surface is in continuous contact with the jacket.

5. The method of claim 1, wherein the core member has a first susceptibility and the marker has a second susceptibility that is different from the first susceptibility.

6. The method of claim 5, wherein the core member and the marker are formed of the same material.

7. The method of claim 5, wherein the marker is disposed on the outer surface.

8. The method of claim 5, wherein the jacket has a thickness; and wherein the marker is disposed within the thickness of the jacket.

9. The method of claim 5, wherein the marker comprises a circumferential band disposed around the core member.

10. The method of claim 5, wherein the core member and the marker are formed of different materials.

11. The method of claim 10, wherein the core member comprises a nickel-titanium alloy and the marker comprises a stainless steel alloy.

12. The method of claim 5, wherein the step of operating the scanner and the step of obtaining the magnetic resonance image are performed while the step of advancing the wire guide distal end through said body vessel is performed.

13. The method of claim 12, wherein the steps of operating the scanner and obtaining the magnetic resonance image are performed multiple times while the step of advancing the wire guide distal end through said body vessel is performed.

14. The method of claim 1, wherein the core member has a proximal end having a proximal end terminal surface fully covered by the jacket and a distal end having a distal end terminal surface fully covered by the jacket.

15. The method of claim 4, wherein the jacket has a jacket proximal end in contact with the proximal end terminal surface of the core member and a jacket distal end in contact with the distal end terminal surface of the core member.

16. A method of performing interventional medical treatment under MRI, said method comprising:

placing a portion of a patient within an MRI system having a scanner such that a portion of a body vessel is located within the scanner;

grasping a wire guide having a wire guide proximal end and a wire guide distal end and comprising a continuous core member, a continuous jacket disposed over and fully encapsulating the entire core member, and a marker disposed on the core member, the core member formed of a first metallic material and having a first length and an outer surface in contact with the jacket, the first length being between 50 centimeters and 350 centimeters, the jacket disposed over the marker and having a second length that is greater than the first length, and the marker formed of a second metallic material;

inserting the wire guide distal end into said body vessel;

advancing the wire guide distal end through said body vessel until the wire guide distal end is disposed at a first position within a first portion of said body vessel that is located within the scanner of the MRI system;

grasping a medical device having a medical device proximal end and a medical device distal end and comprising an elongate member defining a lumen;

passing the medical device distal end over the wire guide proximal end to dispose the wire guide proximal end within the lumen of the elongate member of the medical device;

advancing the medical device distal end over the wire guide and into said body vessel until the medical device distal end reaches a point of treatment within said body vessel;

manipulating the medical device proximal end to produce a manipulation of the medical device distal end at the point of treatment;

operating the scanner of the MRI system to scan the portion of the patient that is positioned within the scanner and that includes the first portion of the body vessel;

obtaining a magnetic resonance image of the first portion of the body vessel;

withdrawing the medical device from the body vessel; and withdrawing the wire guide from the body vessel.

17. The method of claim 13, wherein the core member has a first susceptibility and the marker has a second susceptibility that is different from the first susceptibility.

18. The method of claim 13, wherein the core member and the marker are formed of the same material.

19. The method of claim 16, wherein the core member and the marker are formed of different materials.

20. The method of claim 19, wherein the core member comprises a nickel-titanium alloy and the marker comprises a stainless steel alloy.

\* \* \* \* \*